(12) United States Patent
Henderson et al.

(10) Patent No.: US 9,629,606 B2
(45) Date of Patent: Apr. 25, 2017

(54) PORTABILITY ENHANCING HARDWARE FOR A PORTABLE ULTRASOUND SYSTEM

(71) Applicant: EDAN INSTRUMENTS, INC., Shenzhen (CN)

(72) Inventors: Richard Henderson, Sunnyvale, CA (US); Sean Murphy, Sunnyvale, CA (US)

(73) Assignee: EDAN INSTRUMENTS, INC., Shenzhen (CN)

(*) Notice: Subject to any disclaimer, the term of this patent is extended or adjusted under 35 U.S.C. 154(b) by 0 days.

(21) Appl. No.: 14/825,984

(22) Filed: Aug. 13, 2015

(65) Prior Publication Data
US 2016/0049066 A1 Feb. 18, 2016

Related U.S. Application Data

(60) Provisional application No. 62/037,517, filed on Aug. 14, 2014.

(51) Int. Cl.
*G08B 21/00* (2006.01)
*A61B 8/00* (2006.01)

(52) U.S. Cl.
CPC .................... *A61B 8/4427* (2013.01)

(58) Field of Classification Search
CPC .................................................. A61B 8/4427
USPC ......................................................... 340/679
See application file for complete search history.

(56) References Cited

U.S. PATENT DOCUMENTS

| 5,596,261 | A | * | 1/1997 | Suyama | B60L 11/1803 |
| | | | | | 320/109 |
| 6,067,224 | A | | 5/2000 | Nobuchi | |
| 6,471,651 | B1 | | 10/2002 | Hwang et al. | |
| 6,491,630 | B1 | | 12/2002 | Saccardo et al. | |
| 7,352,570 | B2 | | 4/2008 | Smith et al. | |
| 8,482,259 | B2 | | 7/2013 | Mueller | |
| 9,074,736 | B2 | * | 7/2015 | Recker | F21K 9/13 |
| 2003/0090473 | A1 | | 5/2003 | Joshi | |
| 2004/0215408 | A1 | | 10/2004 | Lamer et al. | |
| 2005/0251035 | A1 | | 11/2005 | Wong et al. | |

(Continued)

FOREIGN PATENT DOCUMENTS

CN 105877781 A * 8/2016 .......... A61B 8/4427

OTHER PUBLICATIONS

International Search Report and Written Opinion issued in related International Patent Application No. PCT/US2015/045088, dated Jul. 14, 2016.

(Continued)

*Primary Examiner* — Nader Bolourchi
(74) *Attorney, Agent, or Firm* — Gilberto M. Villacorta; Brett P. Belden; Foley & Lardner LLP

(57) ABSTRACT

A method for displaying status information related to a portable device includes detecting a portion of a user in a detection zone using a proximity sensor, determining, using a control circuit, that the portable device is in a powered off or power saving state, acquiring, using the control circuit, information about the portable device while the portable device remains in the powered off or power saving state, and displaying, using a system status indicator controlled by the control circuit, a representation of the information about the portable device. The detection zone is defined in relation to a handle of the portable device.

15 Claims, 27 Drawing Sheets

(56) References Cited

U.S. PATENT DOCUMENTS

2009/0043203 A1 2/2009 Pelissier et al.
2010/0262012 A1 10/2010 Wu

OTHER PUBLICATIONS

U.S. Appl. No. 14/825,939, filed Aug. 13, 2015, Henderson et al.
U.S. Appl. No. 14/794,645, filed Jul. 8, 2015, Murphy et al.
International Preliminary Report on Patentability issued in related International Patent Application No. PCT/US2015/045088, dated Feb. 23, 2017.

* cited by examiner

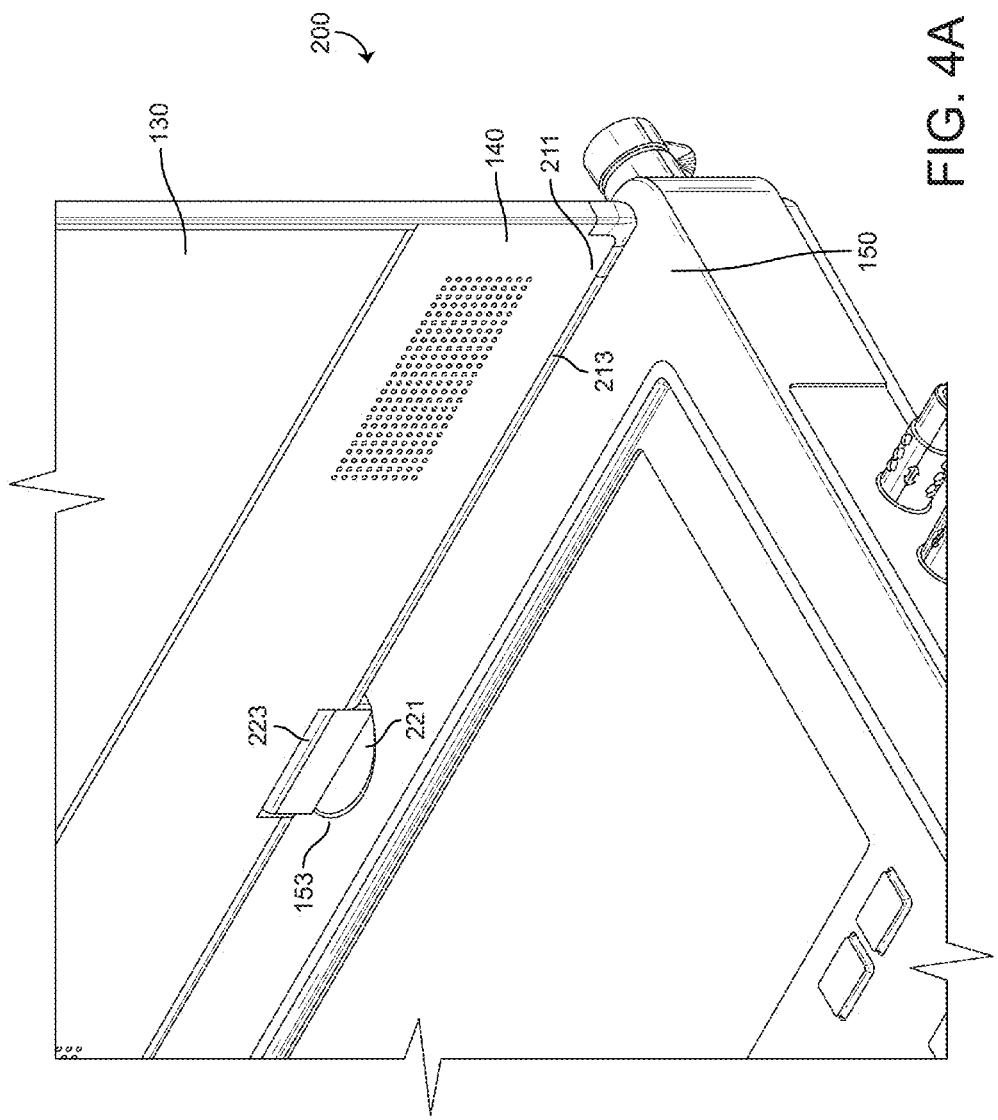

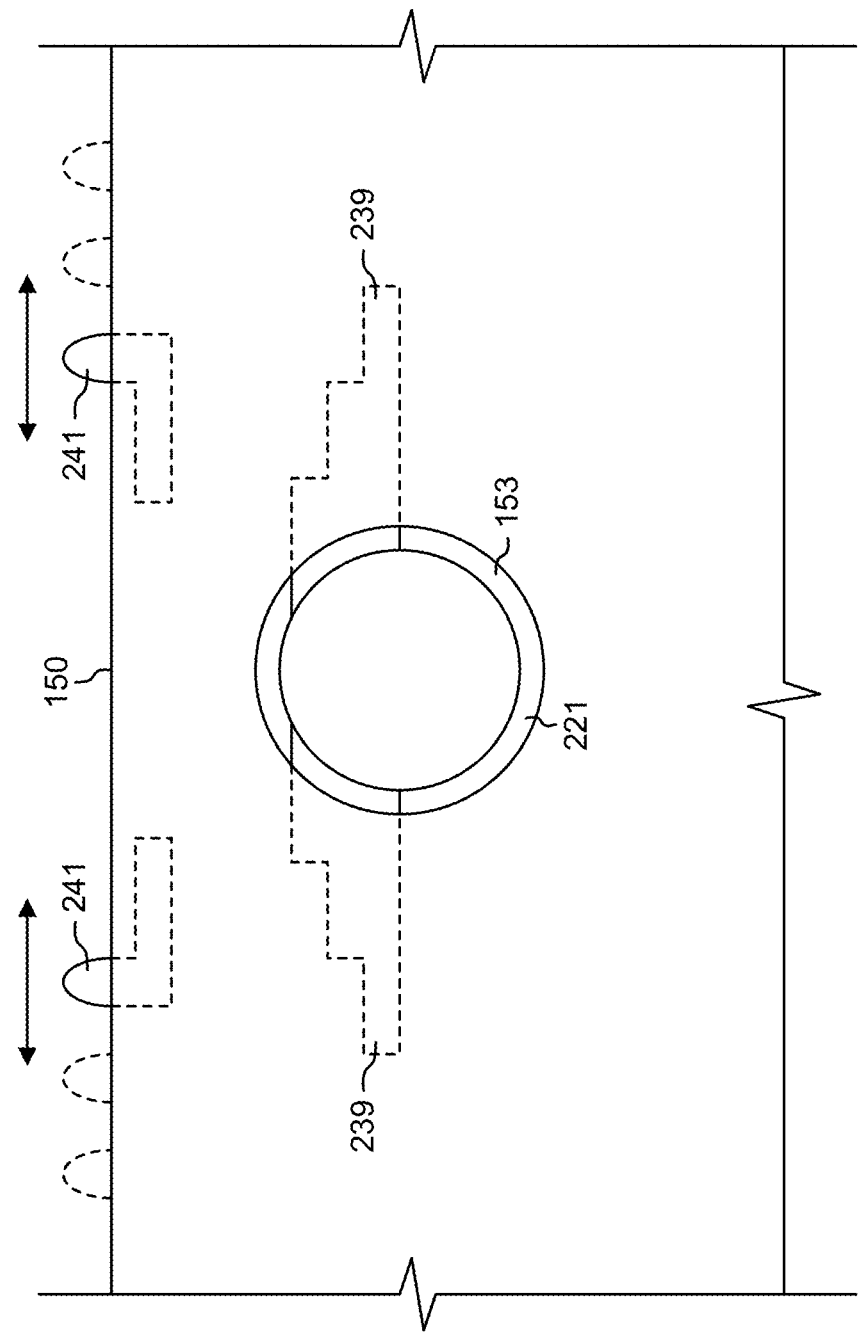

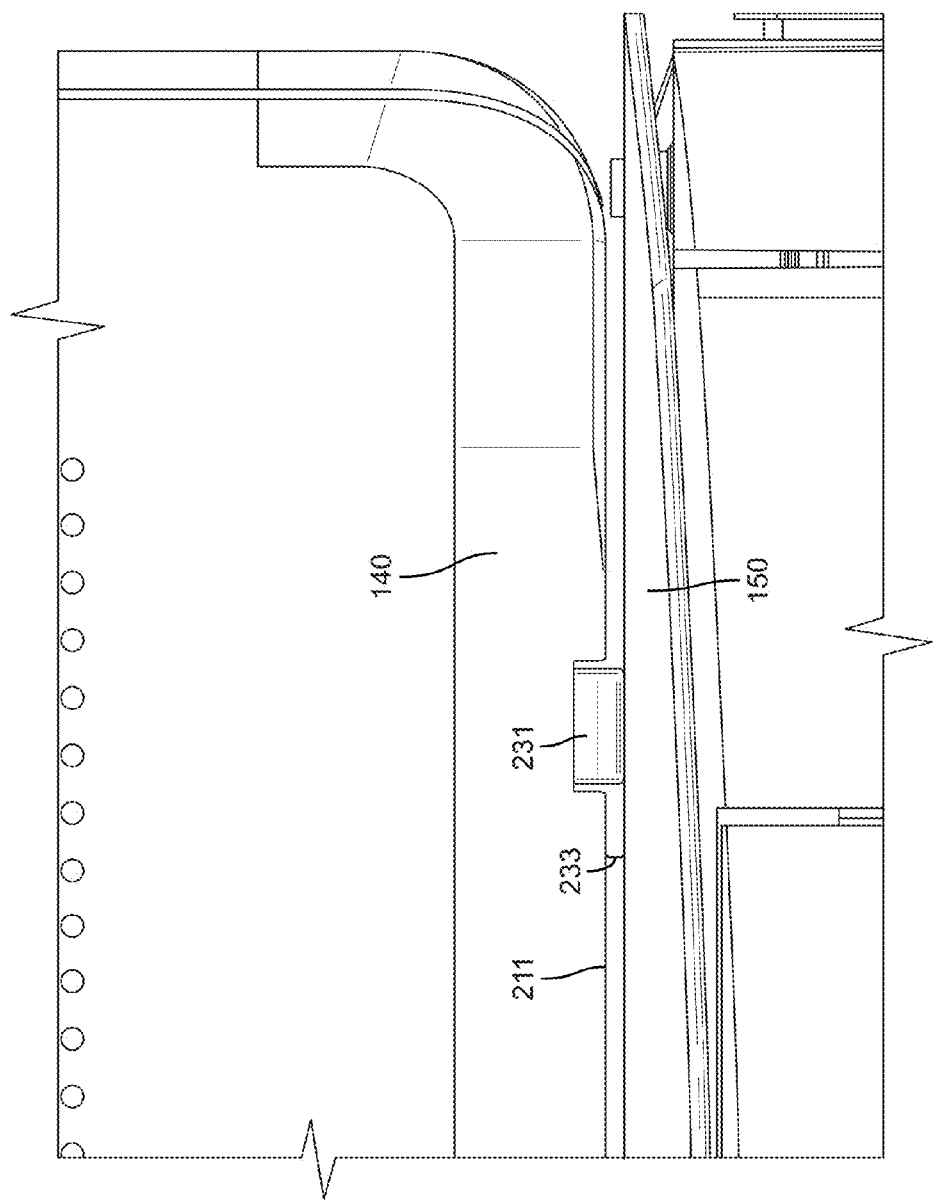

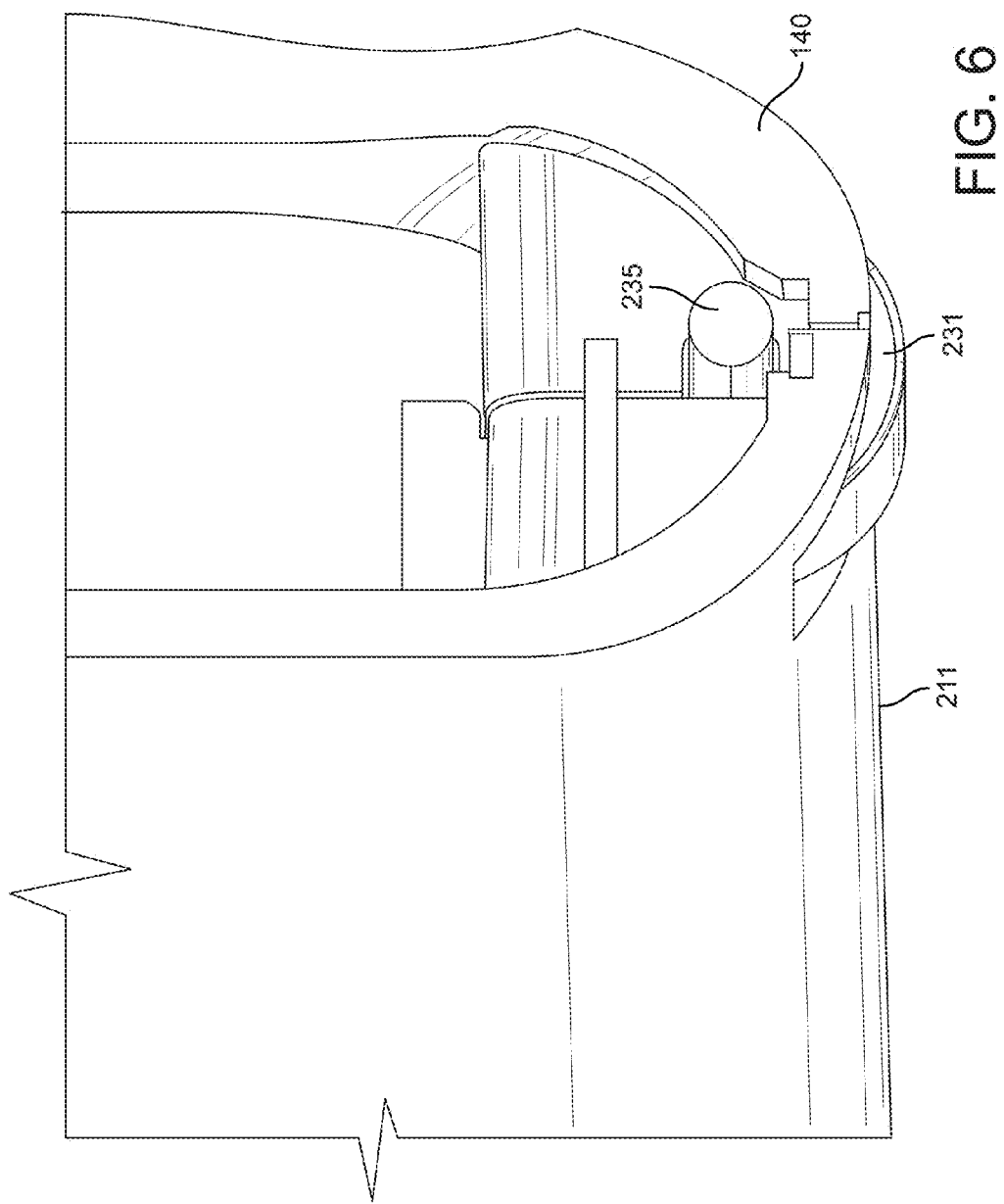

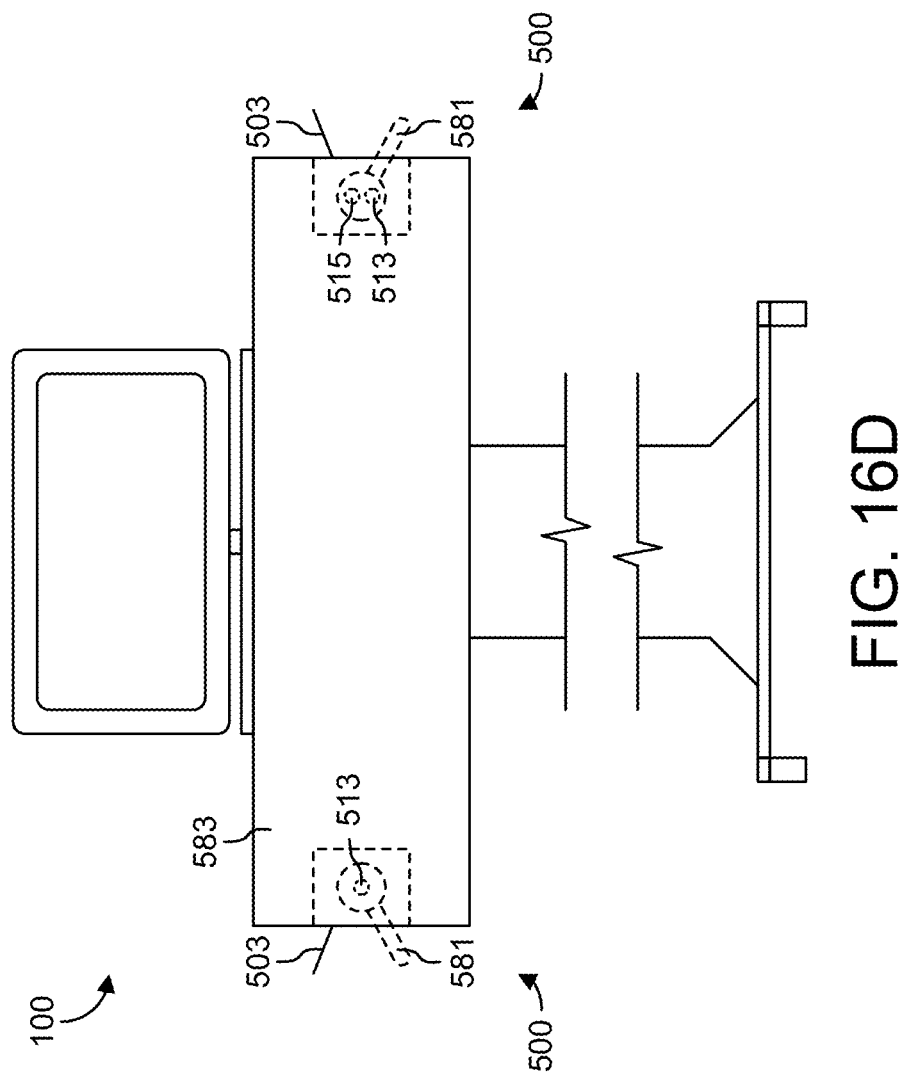

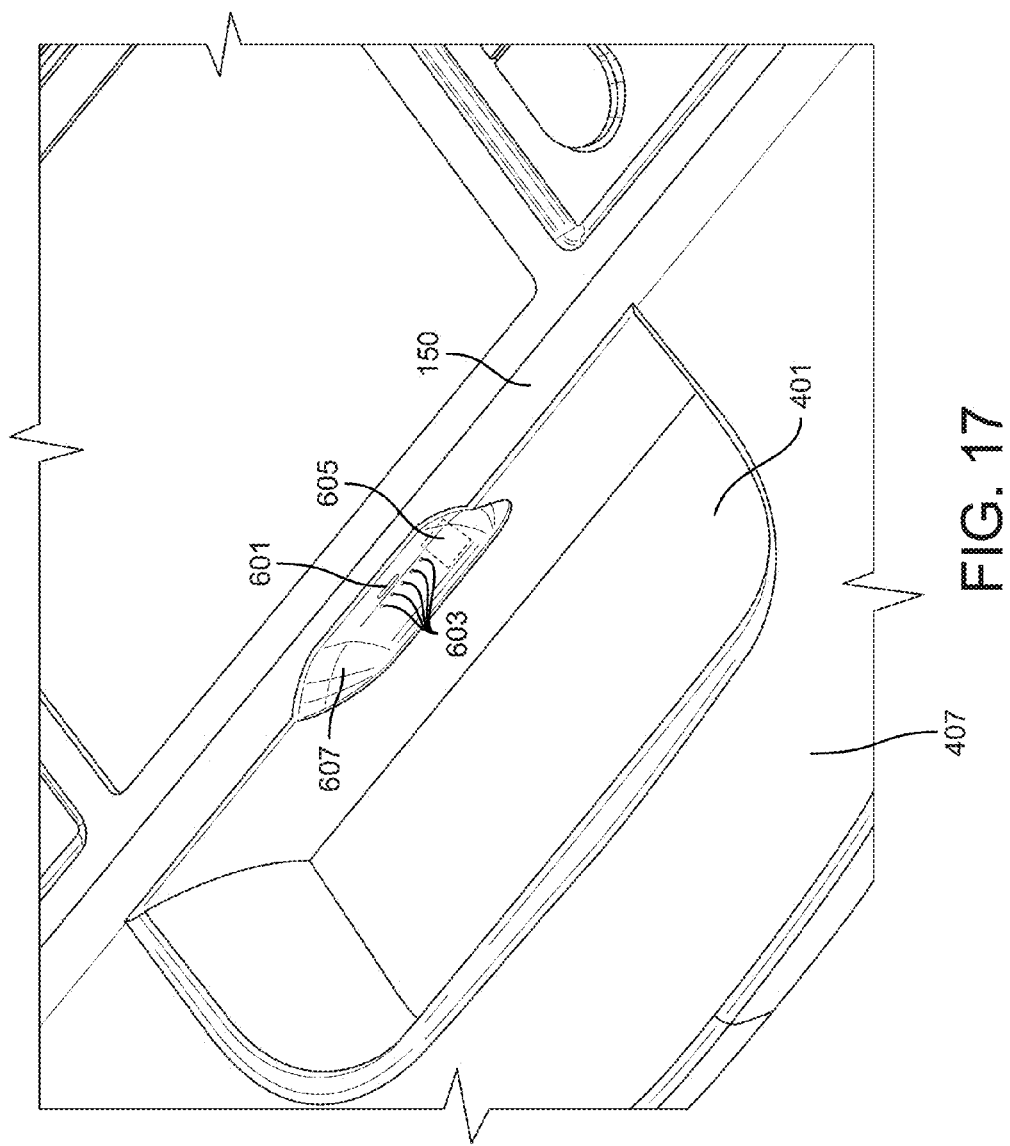

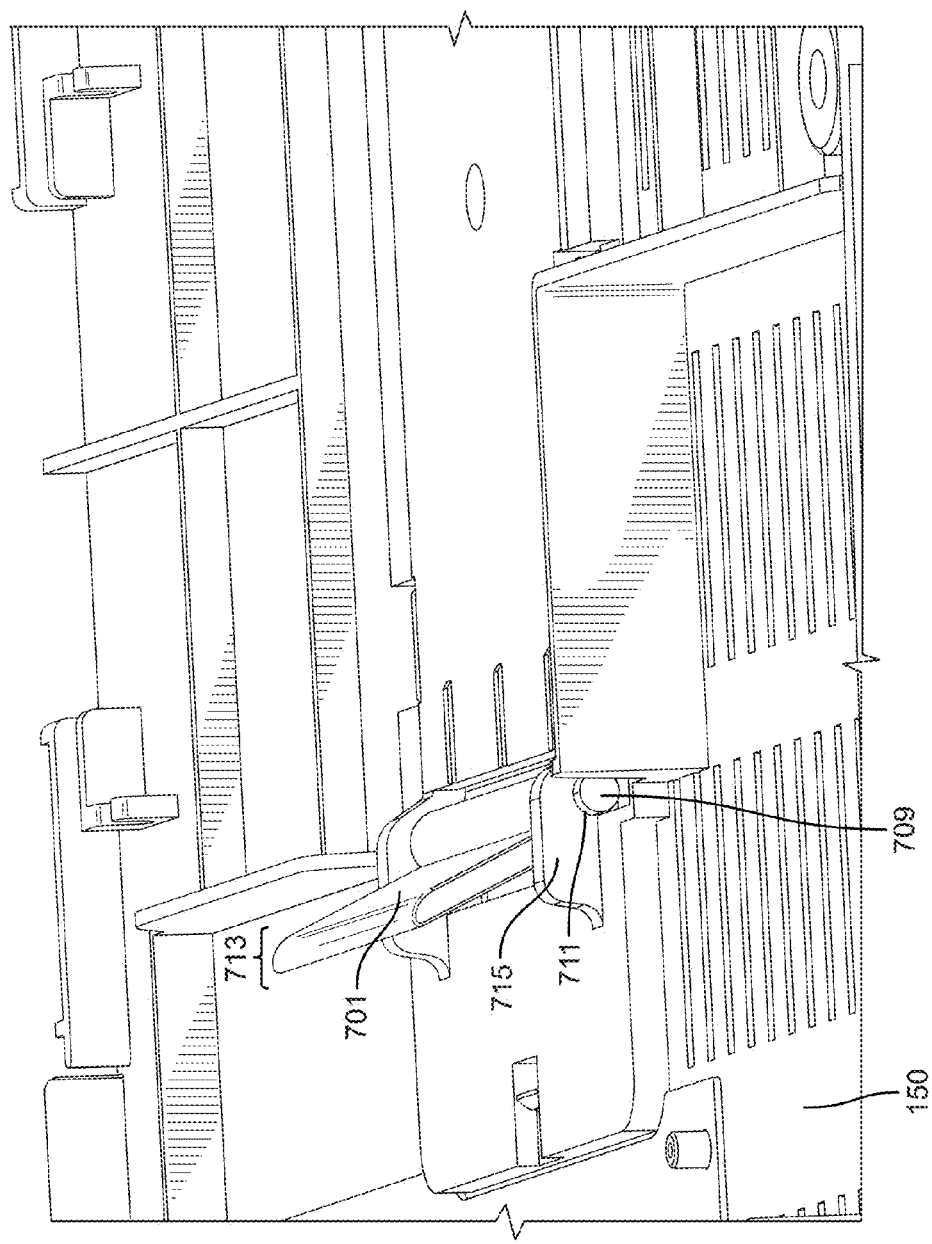

PORTABILITY ENHANCING HARDWARE FOR A PORTABLE ULTRASOUND SYSTEM

CROSS-REFERENCE TO RELATED APPLICATION

This application claims priority from U.S. Provisional Patent Application No. 62/037,517, filed Aug. 14, 2014, which is hereby incorporated by reference in its entirety.

BACKGROUND

The present invention relates generally to the field of portable ultrasound devices. Ultrasound devices image a patient by producing an emitting ultrasonic waves with a transducer. The transducer measures returning echoes of these waves to provide data regarding the patient. The data may be analyzed and assembled into an image of the patient using a computing device. Typically, portable ultrasound devices are large systems transported on a cart with limited battery life. Alternatively, some portable ultrasound systems are hand-held but still relatively large. The present invention includes features which enhance the portability, usability, and configurability of portable ultrasound systems.

SUMMARY OF THE INVENTION

One embodiment relates to a method for displaying status information related to a portable device includes detecting a portion of a user in a detection zone using a proximity sensor, determining, using a control circuit, that the portable device is in a powered off or power saving state, acquiring, using the control circuit, information about the portable device while the portable device remains in the powered off or power saving state, and displaying, using a system status indicator controlled by the control circuit, a representation of the information about the portable device. The detection zone is defined in relation to a handle of the portable device.

Another embodiment relates to a portable device including a proximity sensor having a detection zone defined in relation to a handle of the portable device, a system status indicator configured to display information, and a control circuit coupled to the proximity sensor and the system status indicator. The control circuit is configured to receive input from the proximity sensor indicating that a portion of a user has been detected in the detection zone, determine that the portable device is in a powered off or power saving state, acquire information about the portable device or a subsystem thereof while the portable device remains in the powered off or power saving state, and display a representation of the acquired information via the system status indicator.

Another embodiment relates to a display system for a portable device including a display housing, a main screen contained at least partially within the display housing, and a swivel mechanism including a tilt hinge connected to the display housing such that the display housing can tilt relative to the swivel mechanism and a portion configured to be partially contained in and/or secured to a main housing of the portable device such that the swivel mechanism can rotate relative to the main housing. The display system further includes a wheel partially coupled to the display housing, partially contained within the display housing, and positioned relative to the display housing such that the wheel contacts the main housing through at least a portion of a range in which the swivel mechanism is capable of rotating relative to the main housing.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 4A illustrates an isometric view of the display support system according to one embodiment.

FIG. 4B illustrates swivel mechanism having an adjustable degree of rotation according to one embodiment.

FIG. 5B illustrates close up view of one embodiment of the display support system which includes wheels.

FIG. 6 illustrates a side cross section view of one embodiment of the display support system showing the connection of a wheel to a display housing.

FIG. 16D illustrates a front view of a portable ultrasound system and cart including a conventional locking lever system and a locking lever system with counter rotating gears according to one embodiment.

FIG. 17 illustrates an embodiment of the portable ultrasound device having a status indicator system.

FIG. 22 illustrates a release lever for removing an ultrasound module according to one embodiment.

DETAILED DESCRIPTION

Generally, the invention relates features for a portable ultrasound system. The features enhance the portability, configurability, and functionality of the portable ultrasound system. A portable ultrasound system is typically battery powered. The system may also be powered by mains power when available. The portable ultrasound system may be used for obstetrical and gynecological imaging (e.g., measuring the size of a fetus, checking the position of a fetus, etc.), cardiac imaging (e.g., identifying abnormal heart structures, measuring blood flow, etc.), urological imaging, pulmonology examinations, imaging with abdominal sonography, and/or other ultrasound applications. As portable ultrasound systems may be used in less than ideal conditions (e.g., no ready access to power, no formal work station, etc.), the features described herein help to address the problems associated with such use.

Figure 1:
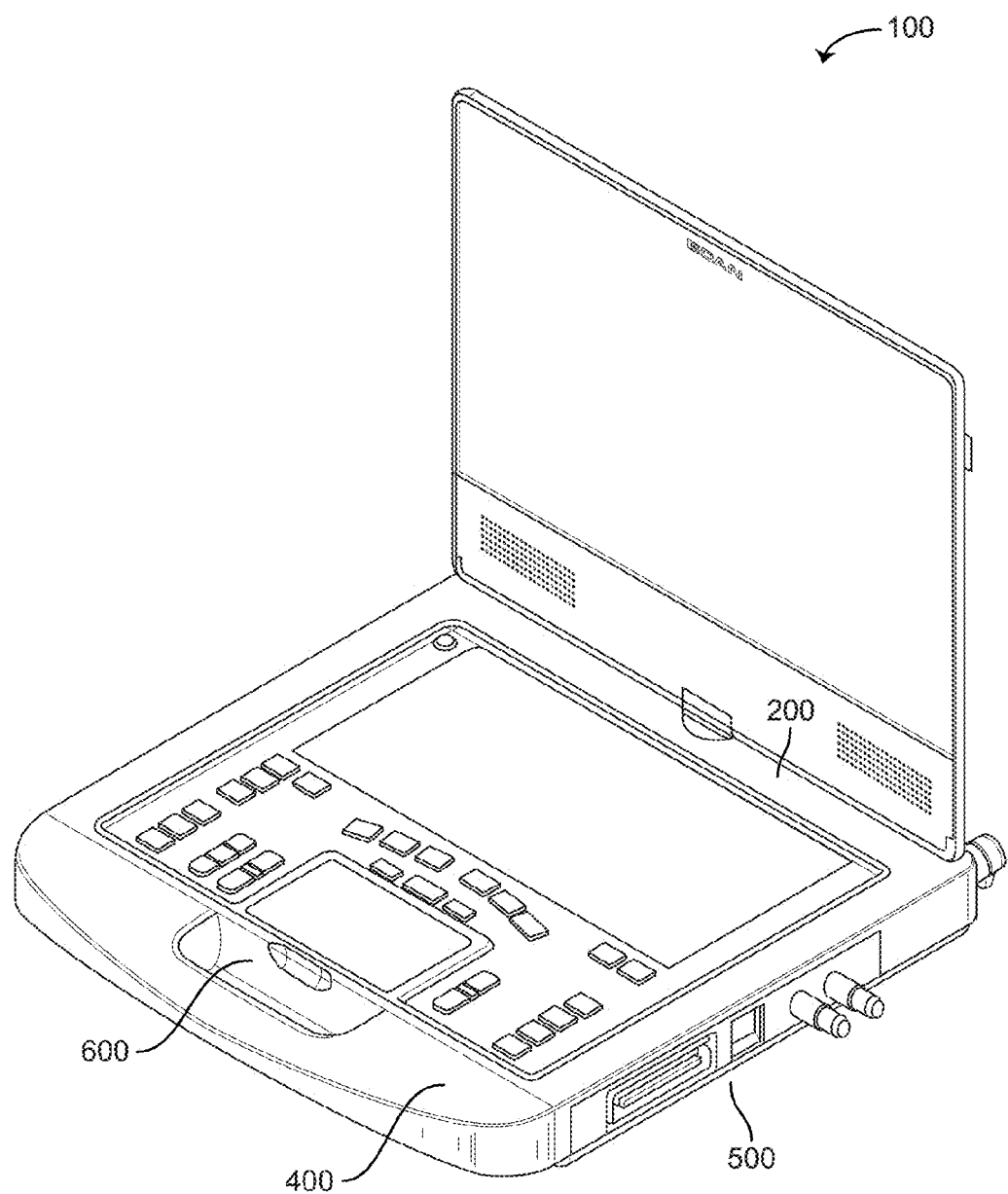
FIG. 1 illustrates an embodiment of a portable ultrasound system incorporating aspects of the invention.

Referring to FIG. 1, one embodiment of portable ultrasound system 100 is illustrated. Portable ultrasound system 100 may include display support system 200 for increasing the durability of the display system. Portable ultrasound system 100 may further include locking lever system 500 for securing ultrasound probes and/or transducers. Some embodiments of portable ultrasound system 100 include ergonomic handle system 400 for increasing portability and usability. Further embodiments include status indicator system 600 which displays, to a user, information relevant to portable ultrasound system 100. Portable ultrasound system 100 may further include features such as an easy to operate and customizable user interface, adjustable feet, a battery, one or more backup batteries, modular construction, cooling systems, etc.

Figure 2:
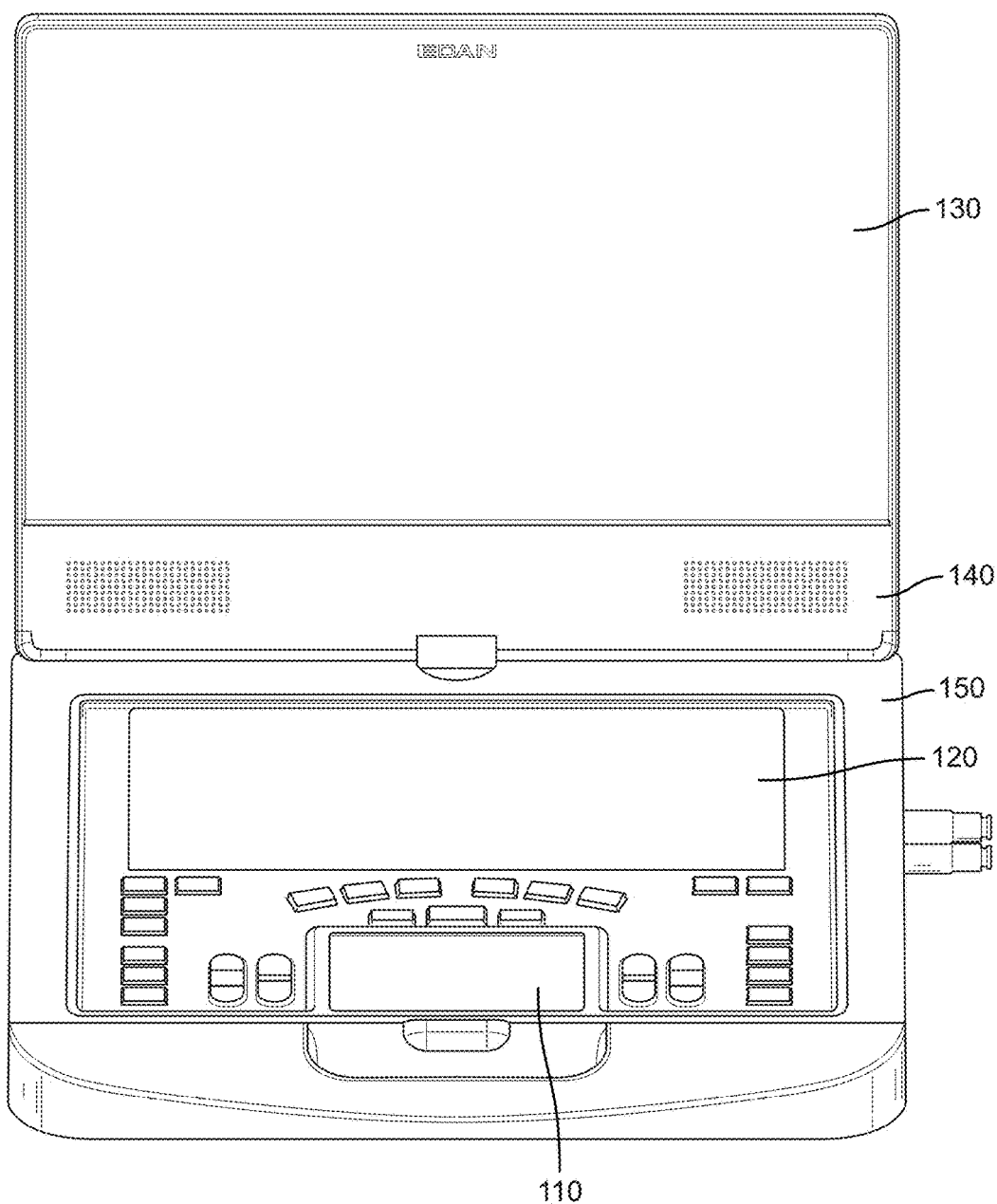
FIG. 2 illustrates a front view of one embodiment of a portable ultrasound system.

Referring to FIG. 2, a front view of one embodiment of portable ultrasound system 100 is illustrated. Main housing 150 houses components of portable ultrasound system 100. In some embodiments, the components housed within main housing 150 include locking lever system 500, ergonomic handle system 400, and status indicator system 600. Main housing 150 may also be configured to support electronics modules which may be replaced and/or upgraded due to the modular construction of portable ultrasound system 100. In some embodiments, portable ultrasound system 100 includes display housing 140. Display housing 140 may include display support system 200. In some embodiments, portable ultrasound system 100 includes touchscreen 110 for receiving user inputs and displaying information, touchscreen 120 for receiving user inputs and displaying information, and main screen 130 for displaying information.

Figure 3A:
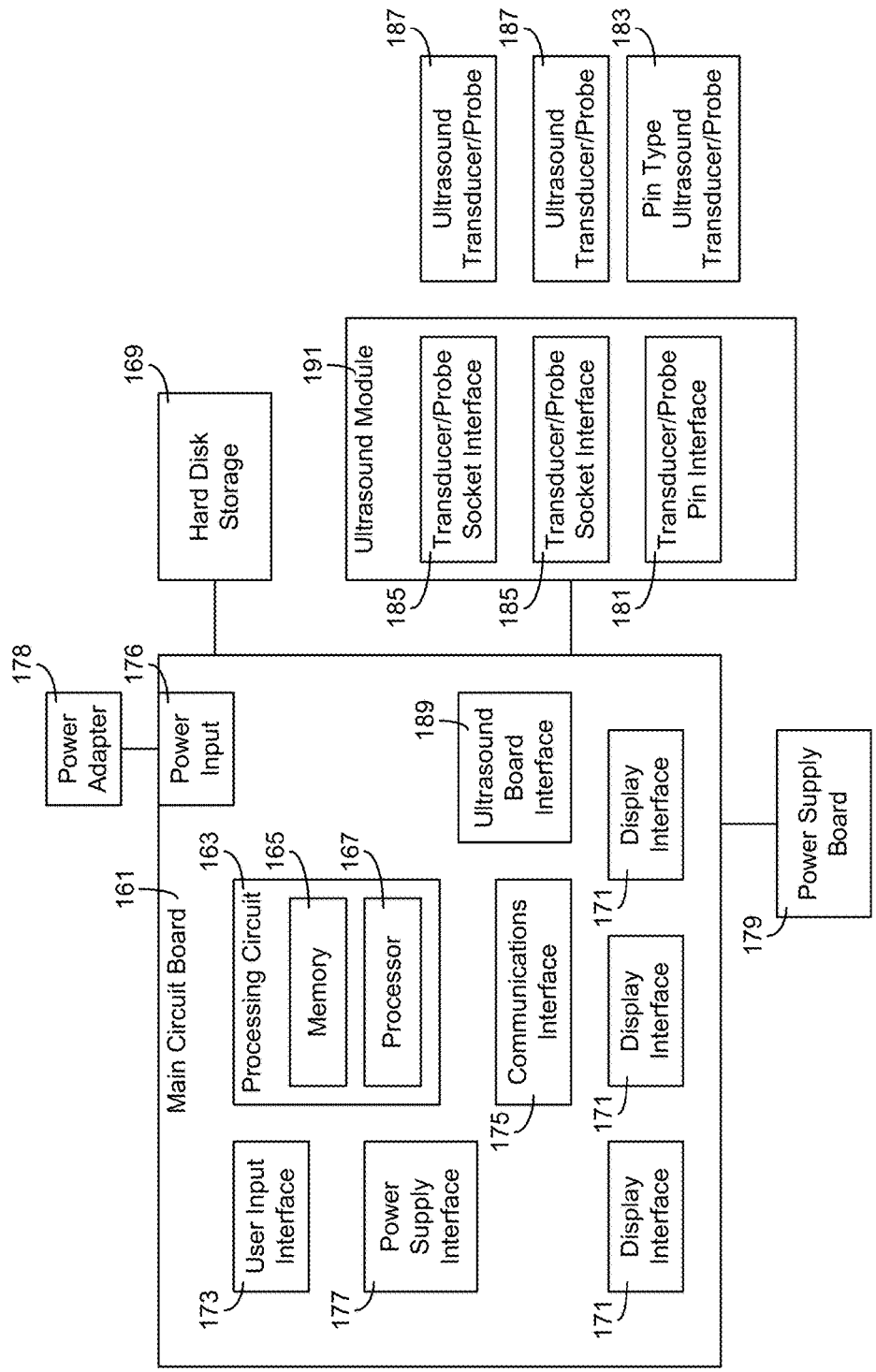
FIG. 3A illustrates a block diagram of components of one embodiment of a portable ultrasound system.

Referring to FIG. 3A, a block diagram shows internal components of one embodiment of portable ultrasound system 100. Portable ultrasound system 100 includes main circuit board 161. Main circuit board 161 carries out computing tasks to support the functions of portable ultrasound system 100 and provides connection and communication between various components of portable ultrasound system 100. In some embodiments, main circuit board 161 is configured so as to be a replaceable and/or upgradable module.

To perform computational, control, and/or communication tasks, main circuit board 161 includes processing circuit 163. Processing circuit 163 is configured to perform general processing and to perform processing and computational tasks associated with specific functions of portable ultrasound system 100. For example, processing circuit 163 may perform calculations and/or operations related to producing an image from signals and or data provided by ultrasound equipment, running an operating system for portable ultrasound system 100, receiving user inputs, etc. Processing circuit 163 may include memory 165 and processor 167 for use in processing tasks. For example, processing circuit may perform calculations and/or operations.

Processor 167 may be, or may include, one or more microprocessors, application specific integrated circuits (ASICs), circuits containing one or more processing components, a group of distributed processing components, circuitry for supporting a microprocessor, or other hardware configured for processing. Processor 167 is configured to execute computer code. The computer code may be stored in memory 165 to complete and facilitate the activities described herein with respect to portable ultrasound system 100. In other embodiments, the computer code may be retrieved and provided to processor 167 from hard disk storage 169 or communications interface 175 (e.g., the computer code may be provided from a source external to main circuit board 161).

Memory 165 can be any volatile or non-volatile computer-readable storage medium capable of storing data or computer code relating to the activities described herein. For example, memory 165 may include modules which are computer code modules (e.g., executable code, object code, source code, script code, machine code, etc.) configured for execution by processor 167. Memory 165 may include computer executable code related to functions including ultrasound imagining, battery management, handling user inputs, displaying data, transmitting and receiving data using a wireless communication device, etc. In some embodiments, processing circuit 163 may represent a collection of multiple processing devices (e.g., multiple processors, etc.). In such cases, processor 167 represents the collective processors of the devices and memory 165 represents the collective storage devices of the devices. When executed by processor 167, processing circuit 163 is configured to complete the activities described herein as associated with portable ultrasound system 100.

Hard disk storage 169 may be a part of memory 165 and/or used for non-volatile long term storage in portable ultrasound system 100. Hard disk storage 169 may store local files, temporary files, ultrasound images, patient data, an operating system, executable code, and any other data for supporting the activities of portable ultrasound device 100 described herein. In some embodiments, hard disk storage is embedded on main circuit board 161. In other embodiments, hard disk storage 169 is located remote from main circuit board 161 and coupled thereto to allow for the transfer of data, electrical power, and/or control signals. Hard disk 169 may be an optical drive, magnetic drive, a solid state hard drive, flash memory, etc.

In some embodiments, main circuit board 161 includes communications interface 175. Communications interface 175 may include connections which enable communication between components of main circuit board 161 and communications hardware. For example, communications interface 175 may provide a connection between main circuit board 161 and a network device (e.g., a network card, a wireless transmitter/receiver, etc.). In further embodiments, communications interface 175 may include additional circuitry to support the functionality of attached communications hardware or to facilitate the transfer of data between communications hardware and main circuit board 161. In other embodiments, communications interface 175 may be a system on a chip (SOC) or other integrated system which allows for transmission of data and reception of data. In such a case, communications interface 175 may be coupled directly to main circuit board 161 as either a removable package or embedded package.

Some embodiments of portable ultrasound system 100 include power supply board 179. Power supply board 179 includes components and circuitry for delivering power to components and devices within and/or attached to portable ultrasound system 100. In some embodiments, power supply board 179 includes components for alternating current and direct current conversion, for transforming voltage, for delivering a steady power supply, etc. These components may include transformers, capacitors, modulators, etc. to perform the above functions. In further embodiments, power supply board 179 includes circuitry for determining the available power of a battery power source. In other embodiments, power supply board 179 may receive information regarding the available power of a battery power source from circuitry located remote from power supply board 179. For example, this circuitry may be included with a battery. In some embodiments, power supply board 179 includes circuitry for switching between power sources. For example, power supply board 179 may draw power from a backup battery while a main battery is switched. In further embodiments, power supply board 179 includes circuitry to operate as an uninterruptable power supply in conjunction with a backup battery. Power supply board 179 also includes a connection to main circuit board 161. This connection may allow power supply board 179 to send and receive information from main circuit board 161. For example, power supply board 179 may send information to main circuit board 161 allowing for the determination of remaining battery power. The connection to main circuit board 161 may also allow main circuit board 161 to send commands to power supply board 179. For example, main circuit board 161 may send a command to power supply board 179 to switch from source of power to another (e.g., to switch to a backup battery while a main battery is switched). In some embodiments, power supply board 179 is configured to be a module. In such cases, power supply board 179 may be configured so as to be a replaceable and/or upgradable module. In some embodiments, power supply board 179 is or includes a power supply unit. The power supply unit may convert AC power to DC power for use in portable ultrasound system 100. The power supply may perform additional functions such as short circuit protection, overload protection, undervoltage protection, etc. The power supply may conform to ATX specification. In other embodiments, one or more of the above described functions may be carried out by main circuit board 161.

Main circuit board 161 may also include power supply interface 177 which facilitates the above described communication between power supply board 179 and main circuit board 161. Power supply interface 177 may include connections which enable communication between components of main circuit board 161 and power supply board 179. In further embodiments, power supply interface 177 includes additional circuitry to support the functionality of power supply board 179. For example, power supply interface 177 may include circuitry to facilitate the calculation of remaining battery power, manage switching between available power sources, providing controlled power to ultrasound module 191, etc. In other embodiments, the above described functions of power supply board 179 may be carried out by power supply interface 177. For example, power supply interface 177 may be a SOC or other integrated system. In such a case, power supply interface 177 may be coupled directly to main circuit board 161 as either a removable package or embedded package.

Main circuit board 161 may also include power input 176. Power input 176 may be hardware and/or software configured to receive electrical power and provide it to one or more components of portable ultrasound system 100. For example, power input 176 can a jack receptacle or other connector for receiving an alternating or direct current power input. For example, the power input may be received from power adaptor 178. Power adaptor 178 may be component external to main housing 150 such a housing and cord. Power adaptor 178 can connect to a mains power supply and removably connect to portable ultrasound system 100 via power input 176 (e.g., a jack receptacle included in power input 176). Power adaptor 178 can perform power conditioning functions such as converting alternating current to direct current, current modulation, power regulation, and/or other functions which alter the electrical power which is provided to power input 176. In further embodiments, power input 176 includes hardware and/or software for receiving electrical power from one or more battery sources. For example, power input 176 can include one or more sets of contacts which electrically and removably couple to electrical contacts included in one or more batteries. In still further embodiments, power input 176 performs power regulating and/or conditioning functions such as those described herein with reference to power adaptor 178, power supply interface 177, and/or power supply board 179

With continued reference to FIG. 3A, some embodiments of main circuit board 161 include user input interface 173. User input interface 173 may include connections which enable communication between components of main circuit board 161 and user input device hardware. For example, user input interface 173 may provide a connection between main circuit board 161 and a capacitive touchscreen, resistive touchscreen, mouse, keyboard, buttons, and/or a controller for the proceeding. In one embodiment, user input interface 173 couples controllers for touchscreen 110, touchscreen 120, and main screen 130 to main circuit board 161. In other embodiments, user input interface 173 includes controller circuitry for touchscreen 110, touchscreen 120, and main screen 130. In some embodiments, main circuit board 161 includes a plurality of user input interfaces 173. For example, each user input interface 173 may be associated with a single input device (e.g., touchscreen 110, touchscreen 120, a keyboard, buttons, etc.).

In further embodiments, user input interface 173 may include additional circuitry to support the functionality of attached user input hardware or to facilitate the transfer of data between user input hardware and main circuit board 161. For example, user input interface 173 may include controller circuitry so as to function as a touchscreen controller. User input interface 173 may also include circuitry for controlling haptic feedback devices associated with user input hardware. In other embodiments, user input interface 173 may be a SOC or other integrated system which allows for receiving user inputs or otherwise controlling user input hardware. In such a case, user input interface 173 may be coupled directly to main circuit board 161 as either a removable package or embedded package.

Main circuit board 161 may also include ultrasound board interface 189 which facilitates communication between ultrasound board 179 and main circuit board 161. Ultrasound board interface 189 may include connections which enable communication between components of main circuit board 161 and ultrasound module 191. In further embodiments, ultrasound board interface 189 includes additional circuitry to support the functionality of ultrasound module 191. For example, ultrasound board interface 189 may include circuitry to facilitate the calculation of parameters used in generating an image from ultrasound data provided by ultrasound module 191. In some embodiments, ultrasound board interface 189 is a SOC or other integrated system. In such a case, ultrasound board interface 189 may be coupled directly to main circuit board 161 as either a removable package or embedded package.

In other embodiments, ultrasound board interface 189 includes connections which facilitate use of a modular ultrasound module 191. Ultrasound module 191 may be a module (e.g., ultrasound module) capable of performing functions related to ultrasound imaging (e.g., multiplexing sensor signals from an ultrasound probe/transducer, controlling the frequency of ultrasonic waves produced by an ultrasound probe/transducer, etc.). Ultrasound module 191 can include one or more ultrasound boards containing hardware and/or software related to ultrasound imaging. For example, ultrasound module 191 can include two ultrasound boards each having 64 channels. This can allow for operation of ultrasound imaging using 64 channels or a total of 128 channels. Ultrasound module 191 can further include additional boards such as an interconnect board. The connections of ultrasound board interface 189 may facilitate replacement of ultrasound module 191 (e.g., to replace ultrasound module 191 with an upgraded board or a board for a different application). For example, ultrasound board interface 189 may include connections which assist in accurately aligning ultrasound module 191 and/or reducing the likelihood of damage to ultrasound module 191 during removal and or attachment (e.g., by reducing the force required to connect and/or remove the board, by assisting, with a mechanical advantage, the connection and/or removal of the board, etc.).

Referring now to FIG. 22, release lever 701 is illustrated according to one embodiment. Release lever 701 facilitates the removal of ultrasound module 191. Release lever 701 extends within main housing 150 as illustrated. A corresponding portion of release lever 701 is accessible from the exterior of main housing 150. This portion can be actuated by a user. When actuated, release lever 701 rotates about axel 709 secured to main housing 150 by opening 711 of flange 715. Release lever 701 may be further secured by additional hardware (e.g., screws, clips, nuts and bolts, and/or other fasteners). Release lever 701 rotates and applies force to ultrasound module 191 (not pictured) which causes ultrasound module 191 to be disconnected from other hardware (e.g., main board 161) and/or partially or ejected from main housing 150. In some embodiments, release lever 701 includes cam portion 713. Cam portion 713 functions as a cam or otherwise controls the force applied to ultrasound module 191 by release lever 701 as release lever 701 is rotated. Advantageously, release lever 701 can disconnect and/or partially eject ultrasound module 191 while providing a mechanical advantage to the user and/or applying force only or substantially only in the direction of ejection. This may reduce wear on ultrasound module 191 and/or reduce the chance of damage to ultrasound module 191 during the ejection process.

Referring again to FIG. 3A, in embodiments of portable ultrasound system 100 including ultrasound module 191, ultrasound module 191 includes components and circuitry for supporting ultrasound imaging functions of portable ultrasound system 100. In some embodiments, ultrasound module 191 includes integrated circuits, processors, and memory. Ultrasound module 191 may also include one or more transducer/probe socket interfaces 185. Transducer/probe socket interface 185 enables ultrasound transducer/probe 187 (e.g., a probe with a socket type connector) to interface with ultrasound module 191. For example, transducer/probe socket interface 185 may include circuitry and/or hardware connecting ultrasound transducer/probe 187 to ultrasound module 191 for the transfer of electrical power and/or data. Transducer/probe socket interface 185 may include hardware which locks ultrasound transducer/probe 187 into place (e.g., a slot which accepts a pin on ultrasound transducer/probe 187 when ultrasound transducer/probe 187 is rotated). In some embodiments, ultrasound module 191 includes two transducer/probe socket interfaces 185 to allow the connection of two socket type ultrasound transducers/probes 187.

In some embodiments, ultrasound module 191 also includes one or more transducer/probe pin interfaces 181. Transducer/probe pin interface 181 enables an ultrasound transducer/probe 187 with a pin type connector to interface with ultrasound module 191. Transducer/probe pin interface 181 may include circuitry and/or hardware connecting ultrasound transducer/probe 187 to ultrasound module 191 for the transfer of electrical power and/or data. Transducer/probe pin interface 181 may include hardware which locks ultrasound transducer/probe 187 into place. In some embodiments, ultrasound transducer/probe 187 is locked into place with locking lever system 500. In some embodiments, ultrasound module 191 includes more than one transducer/probe pin interfaces 181 to allow the connection of two or more pin type ultrasound transducers/probes 187. In such cases, portable ultrasound system 100 may include one or more locking lever systems 500. In further embodiments, ultrasound module 191 may include interfaces for additional types of transducer/probe connections.

With continued reference to FIG. 3A, some embodiments of main circuit board 161 include display interface 171. Display interface 171 may include connections which enable communication between components of main circuit board 161 and display device hardware. For example, display interface 171 may provide a connection between main circuit board 161 and a liquid crystal display, a plasma display, a cathode ray tube display, a light emitting diode display, and/or a display controller or graphics processing unit for the proceeding or other types of display hardware. In some embodiments, the connection of display hardware to main circuit board 161 by display interface 171 allows a processor or dedicated graphics processing unit on main circuit board 161 to control and/or send data to display hardware. Display interface 171 may be configured to send display data to display device hardware in order to produce an image. In some embodiments, main circuit board 161 includes multiple display interfaces 171 for multiple display devices (e.g., three display interfaces 171 connect three displays to main circuit board 161). In other embodiments, one display interface 171 may connect and/or support multiple displays. In one embodiment, three display interfaces 171 couple touchscreen 110, touchscreen 120, and main screen 130 to main circuit board 161.

In further embodiments, display interface 171 may include additional circuitry to support the functionality of attached display hardware or to facilitate the transfer of data between display hardware and main circuit board 161. For example, display interface 171 may include controller circuitry, a graphics processing unit, video display controller, etc. In some embodiments, display interface 171 may be a SOC or other integrated system which allows for displaying images with display hardware or otherwise controlling display hardware. Display interface 171 may be coupled directly to main circuit board 161 as either a removable package or embedded package. Processing circuit 163 in conjunction with one or more display interfaces 171 may display images on one or more of touchscreen 110, touchscreen, 120, and main screen 130.

Figure 3B:
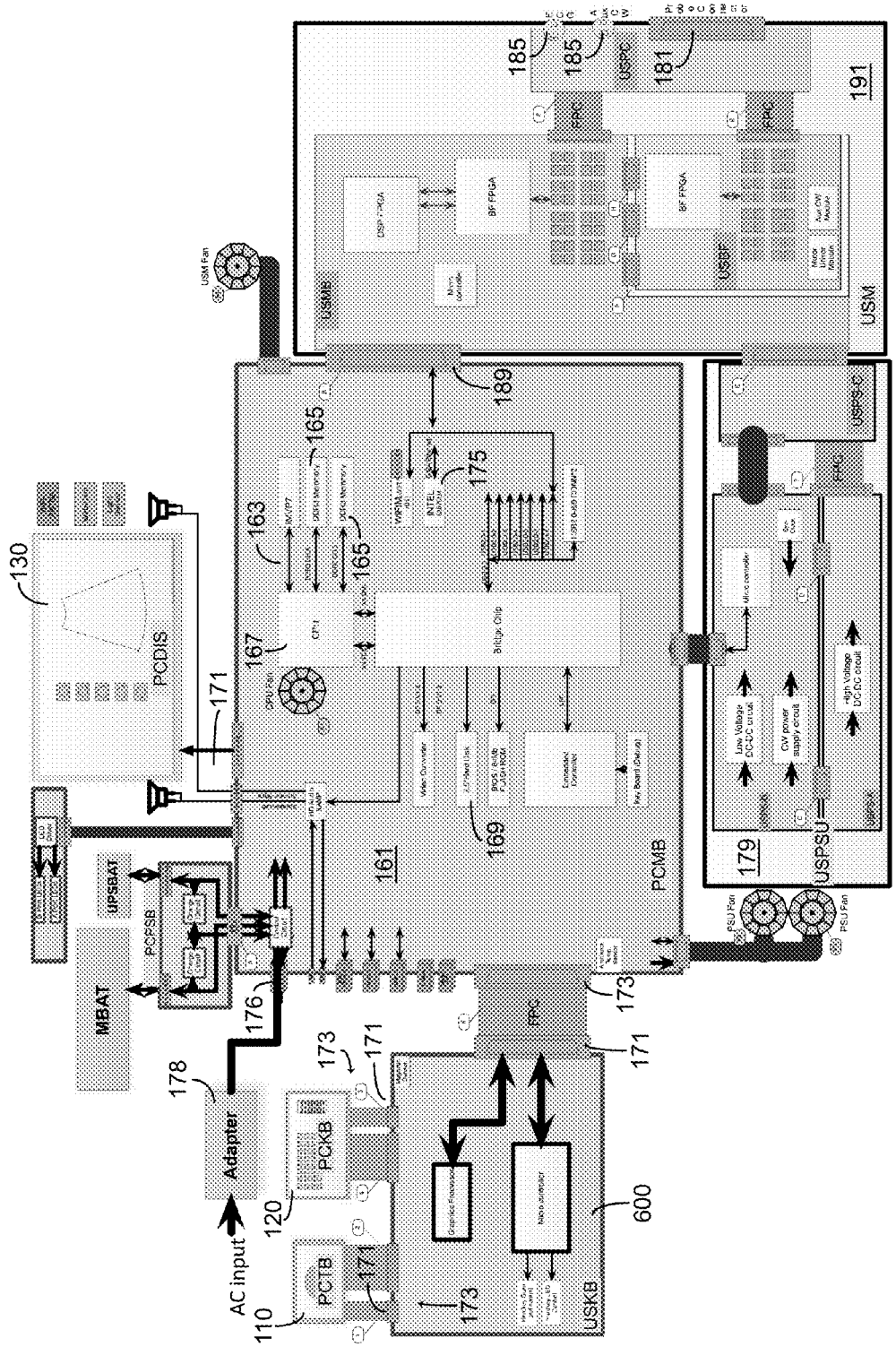
FIG. 3B illustrates a schematic diagram of components included in one embodiment of a portable ultrasound system.

Referring now to FIG. 3B, a schematic diagram of components of portable ultrasound system 100 is illustrated according to one embodiment. Main board 161 (e.g., "PCMB") can include one or more processors 167 and/or memory 165. Processors 167 and memory 165 (e.g., one or more random access memory modules) are used to carry out general computing tasks and/or otherwise support the functions of portable ultrasound system 100 described herein. Main board 161 can further include hard disk storage 169. Hard disk storage can be any storage medium for non-volatile storage of data. For example, hard disk storage 169 can be a 2.5 inch hard disk drive. Main board 161 can further include components which form communications interface 175. For example, main board 161 can include WiFi chips, an Ethernet controller, an Ethernet port, universal serial bus ports, and/or other hardware. Main board 161 can also include audio hardware such as an amplifier or controller as well as audio ports such as 3.5 mm jack port. Main board 161 can further include a motherboard, fan controller, temperature sensors, BIOS chip, and/or other hardware. In some embodiments, main board 161 further includes a control circuit for controlling electrical power sources such as AC adaptor 178 and/or batteries. The control circuit can control functions such as charging the batteries, switching between available power sources, and/or other power control functions. Main board 161 may be coupled to a power control and/or power supply board (e.g., "PCPSB"). The power control and/or power supply board can include circuitry for managing power functions of one or more batteries such as charging circuitry.

Main circuit board 161 is coupled to main screen 130. Main circuit board 161 can be coupled to main screen 130 via one or more connections of a display interface 172. Main screen 130 can be controlled by main circuit board 161 and/or display interface 172. In some embodiments, hardware related to main screen 130 is controlled by main circuit board 161 and/or display interface 172. For example, indicator LEDs, an LED driver, light sensor, camera, WiFi antenna, light sensor, speaker, and/or other hardware can be controlled.

Main circuit board 161 can further be coupled to an input/output control board (e.g., "USKB"). Main circuit board 161 can be coupled to the input/output control board via display interface 171 and/or user input interface 173. The input/output control board can include one or more components of status indicator system 600. For example, the input/output control board can include touch sensors (e.g., a proximity sensor), system status LEDs, battery LEDs, magnetic sensor, control circuitry, and/or other components. The input/output control board can further include graphics processing circuitry (e.g., a graphics processor) for controlling output to one or both of touchscreen 110 and touchscreen 120. Output to touchscreen 110 and/or touchscreen 120 can be achieved using one or more display interfaces 171. Input received from touchscreen 110 and/or touchscreen 120 can be processed using one or more processors and/or other control circuitry or drivers.

Main circuit board 161 is connected to power supply board 179 (e.g., "USPSU"). Power supply board can function as an ultrasound power supply unit. Power supply board 179 can condition power for use by ultrasound module 191 and deliver power to ultrasound module 191. Power supply board 179 can include hardware and/or software such as low voltage direct current converters which perform such functions as providing a low voltage analog power supply, transforming voltage, and/or other power conditioning functions. Power supply board 179 can further include high voltage direct current converts which transform high voltage current and/or otherwise condition power for use by other components. Power supply board 179 can include additional hardware and/or software including power supply circuitry, control circuitry, and/or other components. In some embodiments, power supply board 179 includes a plurality of circuit boards.

Ultrasound module 191 (e.g., "USM") can be coupled to main circuit board 161 and/or power supply board 179. Ultrasound module 191 can include a plurality of circuit boards used to perform ultrasound imaging tasks. Ultrasound module 191 can include two 64 channel ultrasound boards and/or an interconnect board. Ultrasound module 191 can include hardware and/or software such as field programmable gate arrays, control circuitry, temperature sensors, drivers, memory, and/or other components which facilitate and/or perform ultrasound related tasks. Ultrasound module 191 can further include one or more transducer/probe socket interfaces 185 and/or transducer/probe pin interfaces 181. These may be coupled to connectors which allow for connection to transducers/probes of various configurations.

Referring to FIG. 4A, an isometric view of display support system 200 is illustrated according to one embodiment of portable ultrasound system 100. Display support system 200 supports display housing 140 which in turn houses main screen 130. Main housing 150 includes swivel mechanism 221 which protrudes from main housing 150 through main housing opening 153. Swivel mechanism 221 includes tilt hinge 223 which connects swivel mechanism 221 to an axle of display housing 140. Display housing 140 includes display housing edge 211. Display housing edge 211 is the lower edge of display housing 140. In some embodiments, display housing edge 211 may be in contact with main housing 150. In further embodiments, display housing edge 211 may be coated with coating 213 (e.g., to provide friction which eliminates or reduces unintentional movement of display housing 140 or to provide a glide surface).

Referring to FIG. 4A and FIG. 2, the lid of portable ultrasound system 100 (e.g., display housing 140) can be secured in the closed position by magnetic closure in some embodiments. Display housing 140 can be secured in the closed position (e.g., in contact with main housing 150) using magnets rather that a physical latch or other mechanism. Advantageously, this simplifies the opening process as a user does not have to physically manipulate a latch or other mechanical mechanism prior to opening portable ultrasound system 100. Additionally, latches or physical mechanisms which can be visually distracting, catch on hands, arms, or clothing, and/or break due to wear are replaced. Furthermore, openings in display housing 140 and/or main housing 150 which would be used by a mechanical latching system can be eliminated when a magnetic closure system is used. This provides an advantage as removing openings for a latch mechanism reduces the chance of dirt or liquids entering portable ultrasound system 100.

In one embodiment, one or more permanent magnets are included in display housing 140. An additional magnet or ferromagnetic material is included in a corresponding location in main housing 150. When display housing 140 is in the closed position, magnetic attraction between the first magnet and the second magnet or ferromagnetic material keeps display housing 140 securely closed. A user can open portable ultrasound system 100 by applying sufficient force to overcome the magnetic force. In an alternative embodiment, the first magnet is included in main housing 150 and the second magnet or ferromagnetic material is included in display housing 140.

Referring again to FIG. 4A, swivel mechanism 221 allows display housing 140 to rotate about an axis perpendicular to main housing 150. In some embodiments, main housing 150 acts as a flange to secure swivel mechanism 221 to main housing 150. For example, swivel mechanism 221 may include a portion, which is larger than main housing opening 153, located internally to main housing 150. This arrangement may prevent swivel mechanism 221 from separating from main housing 150. In other embodiments, swivel mechanism 221 may be secured to housing 150 using other components in such a way as to allow swivel mechanism 221 to rotate within main housing 150. For example, swivel mechanism 221 may be secured to main housing 150 with one or more of a nut and bolt, interference fit, multiple flanges, etc. In some embodiments, the fit may be selected such that different levels of resistance to rotation exist. The fit may provide resistance in order to keep display housing 140 and swivel mechanism 221 stationary absent an adjustment force from a user. In some embodiments, swivel mechanism 221 is configured to keep display housing edge 211 in contact with main housing 150. In other embodiments, swivel mechanism 221 is configured to prevent display housing edge 211 from contacting main housing 150. In further embodiments, swivel mechanism 221 is configured such that display housing edge 211 contacts main housing 150 at one or more points, but not continuously, during swiveling and/or tilting of the display housing 140.

Referring now to FIG. 4B, a top view of swivel mechanism 221 having an adjustable range of rotation is illustrated according to one embodiments. The amount of display rotation can be adjusted. In one embodiment, the total amount of rotation possible by swivel mechanism 221, and therefore display housing 140 and main screen 130, is user adjustable. Swivel mechanism 221 can include an external appendage (e.g., a lever, pin, screw rod, or other device) which a user can adjust. The external appendage intersects a portion of swivel mechanism 221 during rotation of swivel mechanism 221 to prevent further rotation or limit rotation. Advantageously, a user can limit the range of rotation for a variety of reasons such as limited operational space, ergonomic benefits, personal preference, and/or other reasons.

In one embodiment, swivel mechanism 221 extends below main housing 150 through opening 153. Beneath main housing 150, swivel mechanism includes stepped flanges 239. Stepped flanges are configured to come into contact with an external appendage or other rotation limiting device at different degrees of rotation depending on where the external appendage or other rotation limiting device intersects stepped flanges 239. If the external appendage or other rotation limiting device intersects stepped flanges 239 at the first stepped portion, the rotational range of swivel mechanism 221 will be less than if the external appendage or other rotation limiting device interests stepped flanges 239 at a second or other stepped portion.

In one embodiment, the external appendage is a pair of sliders 241. Sliders 241 can exit main housing 150 such that a user can adjust the position of sliders 241. Sliders 241 have a corresponding portion within main housing 150 configured to intersect stepped flanges 239 depending on the position of sliders 241. Sliders 241 can be moved between several positions such that the point at which sliders 241 intersect with stepped flanges 239 is different at each position. This allows a user to define the maximum range of motion of swivel mechanism 221 using sliders 241. In some embodiments, sliders 241 are independently adjustable. In other embodiments, sliders 241 are linked mechanically such that adjustment of one slider 241 adjusts the other. In alternative embodiments, the external appendage is a different type.

In further alternative embodiments, the range of rotation of swivel mechanism 221 is not user adjustable but can be adjusted during assembly by the use of stop pins. Stop pins can be placed to intersect with the rotation mechanism of swivel mechanism 221 at various locations and therefore define the maximum range of rotation for swivel mechanism 221. In one embodiment, stop pins are placed at various locations to intersect with a specific step of stepped flanges 239. The portion of stepped flange 239 which intersects the stop pin when swivel mechanism 221 is rotated defines the maximum range of rotation for swivel mechanism 221.

Now with continued reference to the embodiment depicted in FIG. 4A, tilt hinge 223 allows display housing 140 to tilt relative to main housing 150. Tilt hinge 223 may allow for the display housing 140 to tilt into a closed position in which display housing 140 covers one or more of touchscreen 120, touchscreen 110, main housing 150, ergonomic handle system 400, and/or a portion of the preceding components. In some embodiments, tilt hinge 223 is configured to keep display housing edge 211 in contact with main housing 150. In other embodiments, tilt hinge 223 is configured to prevent display housing edge 211 from contacting main housing 150. In further embodiments, tilt hinge 223 is configured such that display housing edge 211 contacts main housing 150 at one or more points, but not continuously, during swiveling and/or tilting of the display housing 140. In some embodiments, tilt hinge 223 couples swivel mechanism 221 to display housing 140 such that an axel of display housing 140 allows display housing 140 to rotate within tilt hinge 223. Display housing 140 may provide an axial link between tilt hinge 223 and display housing 140. An axle included within display housing 140 or a separate component secured to display housing 140 may define an axis about which display housing 140 rotates between an open position and a closed position. In some embodiments, the axel is a rod or bar. The axle may extend longitudinally between a first end and a second end, each of which may be attached to display housing 140. In other embodiments, display housing 140 and tilt hinge 223 form a hinge, pivot joint, or other type of bearing providing a rotatable linkage between display housing 140 and tilt hinge 223.

In some embodiments, the fit between tilt hinge 223 and display housing 140 may be selected such that different levels of resistance to rotation exist. The fit may provide resistance in order to keep display housing 140 and tilt hinge 223 stationary absent an adjustment force from a user. For example, the fit may allow display housing 140 to remain stationary at a plurality of angles of rotation relative to main housing 150.

In some embodiments, display housing edge 211 is coated with coating 213. Coating 213 may be in contact with both housing edge 211 and main housing 150. In some embodiments, coating 213 provides friction force to prevent display housing 140 from tilting and/or swiveling relative to main housing 150 absent a user input. In other embodiments, display housing 140 remains in contact with main housing 150. Swivel mechanism 221 and/or tilt hinge 223 may be sized such that display housing 140 remains in contact with main housing 150 at all times or a portion of the range of motion of display housing 140 relative to main housing 150. The contact between display housing 140 and main housing 150 may reduce the force experienced by and/or load carried by swivel mechanism 221 and tilt hinge 223. In some embodiments, coating 213 and the contact between display housing edge 211 and main housing 150 reduces the stress on swivel mechanism 221. In further embodiments, coating 213 and the contact between display housing edge 211 and main housing 150 supports, wholly or partially, display housing 140 such that the display housing 140 remains horizontally stable.

In some embodiments, coating 213 facilitates the contact between display housing 140 and main housing 150. For example, coating 213 may be a friction reducing coating which helps display housing 140 remain in contact with main housing 150 while also facilitating adjustments of the display housing 140 (e.g., reducing friction and therefore the force required to tilt and/or swivel display housing 140). For example, coating 213 may be a polymer with a low coefficient of friction such as polytetrafluoroethylene. In other embodiments, coating 213 provides sufficient friction to keep display housing 140 in place absent a user input while maintaining load transferring contact between display housing 140 and main housing 150. For example, coating 213 may be a polymer with a high coefficient of friction or rubber.

In other embodiments, coating 213 may act as a skid plate. In further embodiments, coating 213 may be applied to main housing 150 in the area in contact with display housing 140. Coating 213 as applied to main housing 150 may perform the same functions as in embodiments when coating 213 is applied to display housing edge 211.

Figure 5A:
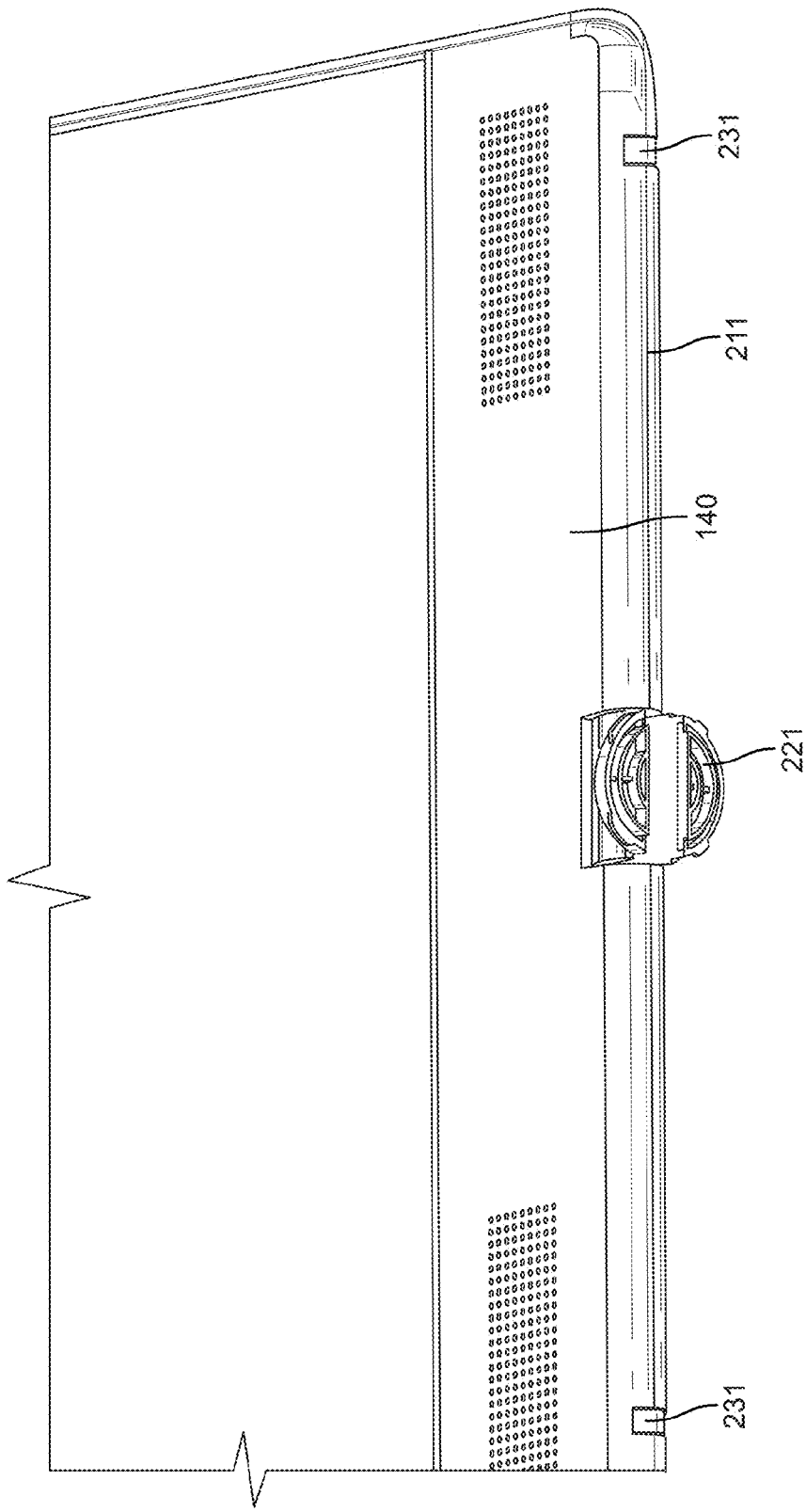
FIG. 5A illustrates an embodiment of the display support system which includes wheels.

FIG. 5A illustrates an embodiment of portable ultrasound system 100 including wheel 231 in display housing 140. In some embodiments, one or more wheels 231 are attached to display housing 140. In the illustrated embodiment, one wheel 231 is placed on either side of swivel mechanism 221. In other embodiments, a plurality of wheels 231 are included on each side of swivel mechanism 221. In further embodiments, one wheel 231 may extend the length of all or a portion of display housing 140 on one side of swivel mechanism 221. Wheels 231 may be configured to transmit force placed on display housing 140 from display housing 140 to main housing 150. This may reduce the force transferred or load carried by swivel mechanism 221 and or tilt hinge 223. In some embodiments, wheels 231 reduce the stress on swivel mechanism 221. In further embodiments, wheels 231 support, wholly or partially, display housing 140 such that the display housing 140 remains horizontally stable. In some embodiments, wheels 231 are made of one or more of plastic, rubber, or polymer.

Referring now to FIG. 5B, wheels 231 may extend beyond display housing edge 211 such that display housing edge 211 does not contact main housing 150 except through wheels 231. In some embodiments, display housing 140 contacts main housing 150 when closed but does not contact main housing 150 when being tilted or swiveled, except through wheels 231 and/or swivel mechanism 221. Wheels 231 may support display housing 140 above main housing 150 such that a gap 233 separates main housing 150 from display housing edge 211. Gap 233 may we widened or narrowed depending on the radius of wheels 231 and/or the configuration of swivel mechanism 221 and/or tilt hinge 223. In some embodiments, the placement of the rotational axis of wheels 231 may also be used to adjust gap 233.

FIG. 6 illustrates a side cross section of an embodiment of display support system 200 which includes wheel 231. Wheel 231 is shown to extend beyond display housing edge 211. Wheel 231 may be supported by wheel axel 235. Wheel axel 235 may, in turn, be coupled to display housing 140. In some embodiments, wheel axel 235 is coupled to display housing 140 such that it is held stationary. For example, wheel axel 235 may be formed as part of display housing 140 through molding techniques. Wheel 231 may rotate freely about wheel axel 235. In other embodiments, wheel 231 is fixed to wheel axel 235. Wheel axel 235 may rotate freely within a support structure built into or coupled to display housing 140. For example, wheel axel 235 may rotate within a bearing assembly coupled to display housing 140.

Figure 7:
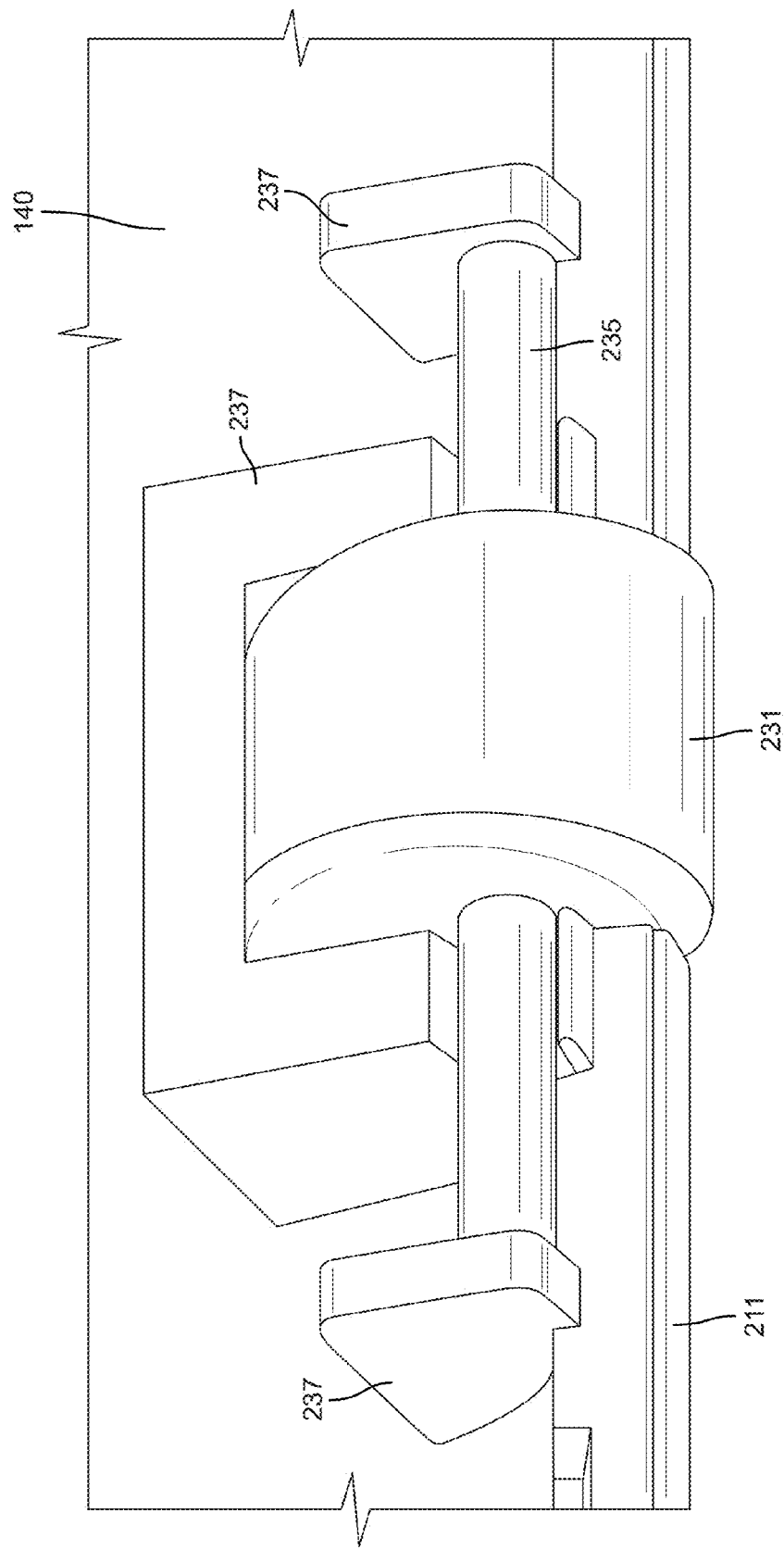
FIG. 7 illustrates a front cross section view of one embodiment of the display support system showing the connection of a wheel to a display housing.

FIG. 7 illustrates a front cross section of an embodiment of display support system 200 which includes wheel 231. Wheel 231 is coupled to wheel axel 235. In some embodiments, wheel 231 is free to rotate about wheel axel 235. In other embodiments, wheel 231 is attached to wheel axel 235 and cannot rotate about wheel axel 235. In the illustrated embodiment, axel support mechanisms 237 support wheel axel 235. Axel support mechanisms 237 are coupled to display housing 140. In some embodiments, axel support mechanisms 237 are formed to be an extrusion or integral part of display housing 140. In other embodiments, axel support mechanisms 237 are attached to display housing 140. For example, axel support mechanisms 237 may be attached to display housing 140 with fasteners, screws, bolts, adhesive, etc.

In some embodiments, wheel axel 235 is held in place by axel support mechanisms 237 and cannot rotate within axel support mechanisms 237. In this case, wheel 231 is free to rotate about wheel axel 235. Axel support mechanisms 237 may hold wheel axel 235 with an interference fit. Axel support mechanisms 237 may also be formed to be a single component with wheel axel 235. In other embodiments, wheel axel 235 is free to rotate within axel support mechanisms 237. Axel support mechanisms 237 may include bearings. Axel support mechanisms 237 may also support wheel axel 235 with a running fit. In this case, wheel 231 may be fixed to wheel axel 235 such that wheel 231 does not rotate relative to wheel axel 235. Wheel 231 may also be allowed to rotate freely about wheel axel 235.

With reference to FIGS. 5A-7, in some embodiments, wheel 231 and the supporting components (e.g., wheel axel 235, wheel support mechanisms 237) illustrated in FIGS. 4A-6 are located within main housing 150. Wheel 231 may protrude from an opening in main housing 150 and contact display housing edge 211. In the manner previously described, wheel 231 and any supporting components may transfer force, load, stress, etc. from display housing 140 to main housing 150. This may reduce the stress on swivel mechanism 221 and/or tilt hinge 223.

The embodiments of display support system 200 described herein with reference to FIGS. 4A-7 enhance the durability of portable ultrasound system 100. As portable ultrasound system 100 may be used in harsh conditions where its portable nature is exploited, durability increases the lifecycle of the device. As explained herein, display support system 200 reduces the stress experienced by components of portable ultrasound system 100 in normal use (e.g., stress on swivel mechanism 221 and tilt hinge 223 due to positioning of display housing 140 and main screen 130 therein). Thus, the life cycle of portable ultrasound system 100 is increased.

Referring generally to FIGS. 4A-8, in some embodiments, display support system 200 does not include wheels 231. In still further embodiments, display support system 200 includes one or more gaps in display housing 140 but does not include wheels 231. Display support system 200 can further include one or more wheel axels 235 and related support structures (e.g., support mechanisms 237). The gap in display housing 140 can be temporarily filled with a plug. Advantageously, the plug provides a more esthetically pleasing appearance, partially or completely seals the gap, and/or prevents contaminants from entering display housing 140. In some embodiments, the plug may be removed and one or more wheels 231 can be added. In further embodiments, manufacturing of portable ultrasound system 100 can be changed to include wheels 231 without changing entirely or at all display housing 140 (e.g., without adding gaps to display housings 140).

Figure 8:
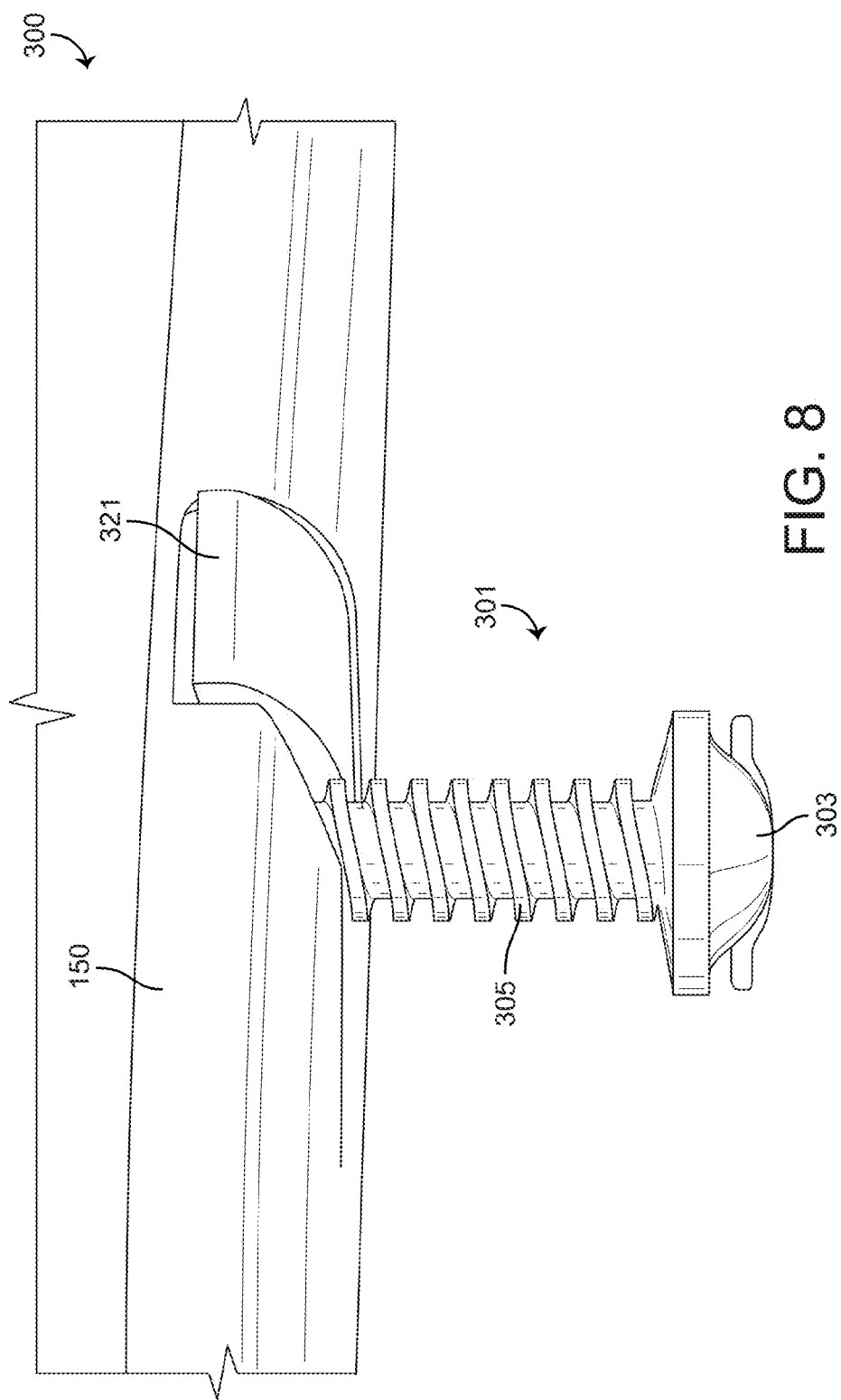
FIG. 8 illustrates an embodiment of the adjustable feet system.

FIG. 8 illustrates an embodiment of portable ultrasound system 100 including an adjustable feet system 300. Portable ultrasound system 100 may rest on feet 301. Feet 301 may be located at one or more of the corners of portable ultrasound system 100. In some embodiments, foot 301 extends from housing 150. Foot 301 may be extended or retracted from main housing 150 to adjust the height and/or angle of portable ultrasound system 100 relative to a surface. In some embodiments, foot 301 includes an adjustment shaft 305 which is threaded. By turning foot 301 clockwise or counterclockwise a user may extend or retract foot 301. The threads advance foot 301 as foot 301 is turned. In some embodiments, foot 301 includes a flange on the end of adjustment shaft 305 within housing 150. The flange is larger than the opening in main housing 150 from which adjustment shaft 305 protrudes. The flange may prevent foot 301 from being inadvertently removed from main housing 150.

In some embodiments, foot 301 is spring loaded such that it extends to meet a surface below foot 301. Foot 301 may be held in place by a threaded locking mechanism which is normally engaged with threaded adjustment shaft 305. By depressing push button 321, a user may disengage the threaded locking mechanism such that spring loaded foot 301 extends to meet a surface below foot 301. When the desired angle and height of portable ultrasound system 100 is achieved, a user may release push button 321 to re-engage the threaded locking mechanism. The foot is then held in place by the threads of the threaded locking mechanism engaging the threads of adjustment shaft 305. Without depressing push button 321, a user may manually adjust the height of foot 301 by turning foot 301 clockwise or counter clockwise as the threaded locking mechanism still allows the foot to be manually advanced via the threads on adjustment shaft 305. Adjustable feet system 300 enhances the portability of portable ultrasound system 100 by allowing a user to quickly and easily position portable ultrasound system 100 at a desired height and/or angle relative to a surface which may be rough or uneven. The user does not have to blindly feel for a foot to make a manual adjustment. Instead the user may push an easily located button to position portable ultrasound system 100 as desired and release the button to lock in the desired position.

In other embodiments, foot 301 may not be spring loaded. Foot 301 may be extended automatically due to the force of gravity. In some embodiments, foot 301 is extended by an electric motor and gear. In some embodiments, depressing push button 321 automatically levels main housing 150. For example, one or more inclinometers may sense the angle of main housing 150 relative to gravity and a circuit may activate one or more electric motors coupled to feet 301 until main housing 150 is level.

In some embodiments, feet 301 are located only at the rear of main housing 150. In other embodiments, feet 301 are located at the four corners of main housing 150. Push button 321 may be located on the side of main housing 150. In some embodiments, push button 321 protrudes from main housing 150. This may enable a user to locate push button 321 by touch. In other embodiments, push button 150 is flush with main housing 150. This may prevent the accidental depressing of push button 321.

In some embodiments, foot 301 includes contact portion 303. Contact portion 303 is the portion of foot 301 which is in contact with the surface beneath portable ultrasound system 100. In some embodiments, contact portion 303 is made of a material to increase comfort. For example, contact portion 303 may be made of rubber. In other embodiments, contact portion 303 is made of a durable material. For example, contact portion 303 may be made of a plastic or metal.

Figure 9:
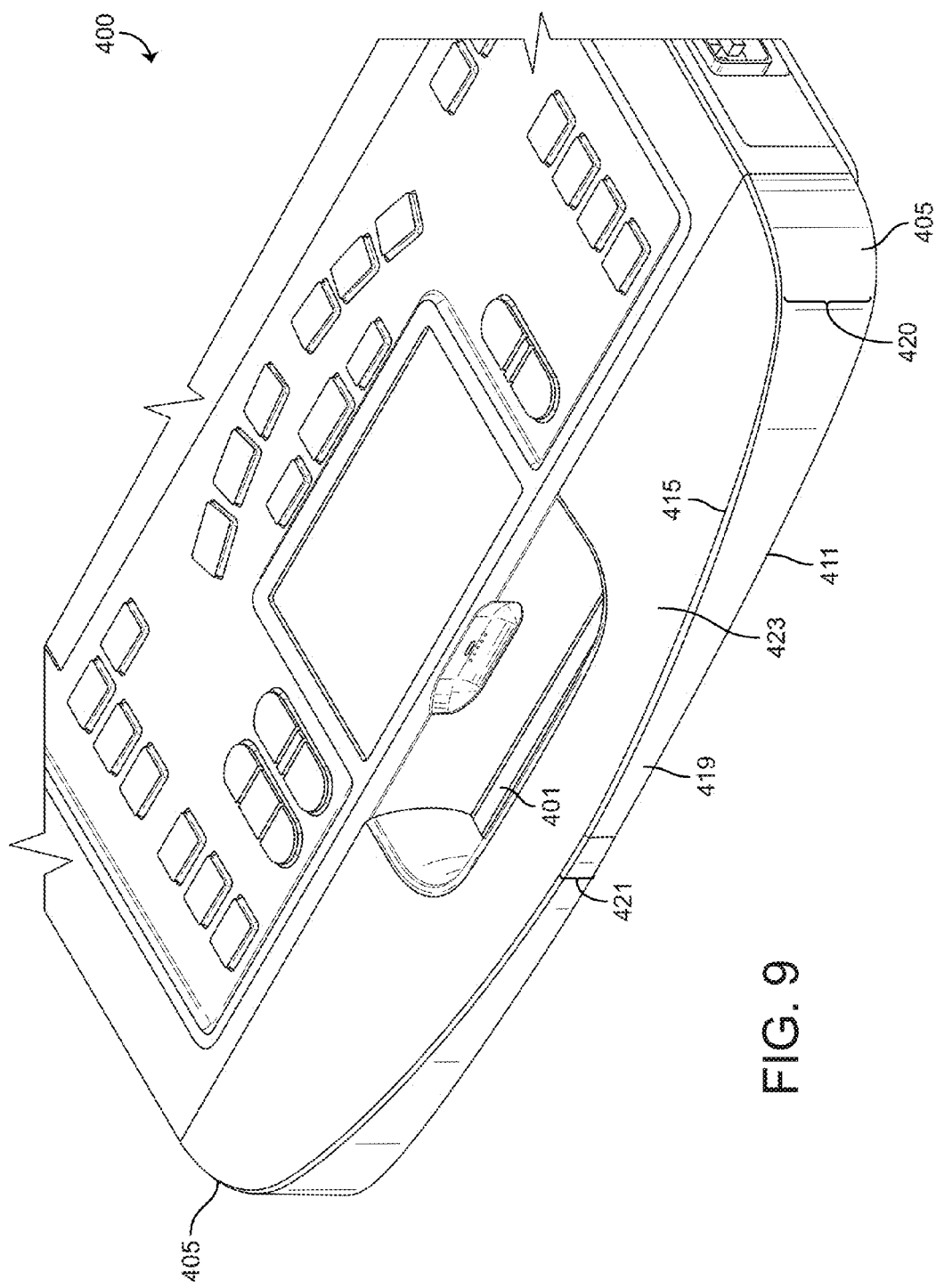
FIG. 9 illustrates an embodiment of the invention including an ergonomic handle system.

FIG. 9 illustrates an embodiment of portable ultrasound system 100 including ergonomic handle system 400. Ergonomic handle system 400 may be comprised of curvilinear forms to increase the comfort of the user. In some embodiments, ergonomic handle system 400 is incorporated into main housing 150. For example, main housing 150 and ergonomic handle system 400 may be formed in a single molding process. In other embodiments, ergonomic handle system 400 may be attached to main housing 150. For example, ergonomic handle system 400 may be attached to main housing 150 with fasteners, screws, nuts and bolts, adhesive, etc. In the illustrated embodiment, ergonomic handle system 400 includes handle cutout 401. Handle cutout 401 provides a space for a user's fingers and/or hand to grip the handle formed by handle cutout 401. In some embodiments, handle cutout 401 may be made of or coated in a gripping material. For example, handle cutout 401 may be coated in rubber. The user's hand wraps around top face 423, front face 419, and bottom face 427. Top face 423 and/or bottom face 427 may be sloped towards handle cutout 401. Similarly the height of front face 419 may decrease from height 420 at the side to height 421 at the midpoint of handle cutout 401. The sloping of top face 423, sloping of bottom face 427, and/or reduction in height of front face 419 may create a section of ergonomic handle system 400 which is easier to grasp in conjunction with handle cutout 401.

In some embodiments, this arrangement of the sloping of top face 423, sloping of bottom face 427, and/or reduction in height of front face 419 creates an arm and/or wrist rest space on top face 423 to accommodate a user's wrists and/or forearms. This may enhance the portability of portable ultrasound system 100 by providing a comfortable use experience when in the field. Top face 423 may form a depression. The slope of top face 423 may be adjusted to improve the comfort or ergonomics of the rest space of top face 423. Upper edge 415 may also be rounded in order to improve the comfort of the rest space created by top face 423. In some embodiments, lower edge 411 is also rounded. The combination of rounded upper edge 415 and rounded lower edge 411 may make grasping the handle created by handle cutout 401 more comfortable for a user.

The illustrated embodiment also includes rounded corners 405. Rounded corners 405 may assist in creating an ergonomic top face 423 for use as an arm and/or wrist rest. Rounded corners 405 may further create a more comfortable carrying experience by reducing the number of sharp edges which may come into contact with a user carrying portable ultrasound system 100.

Figure 10:
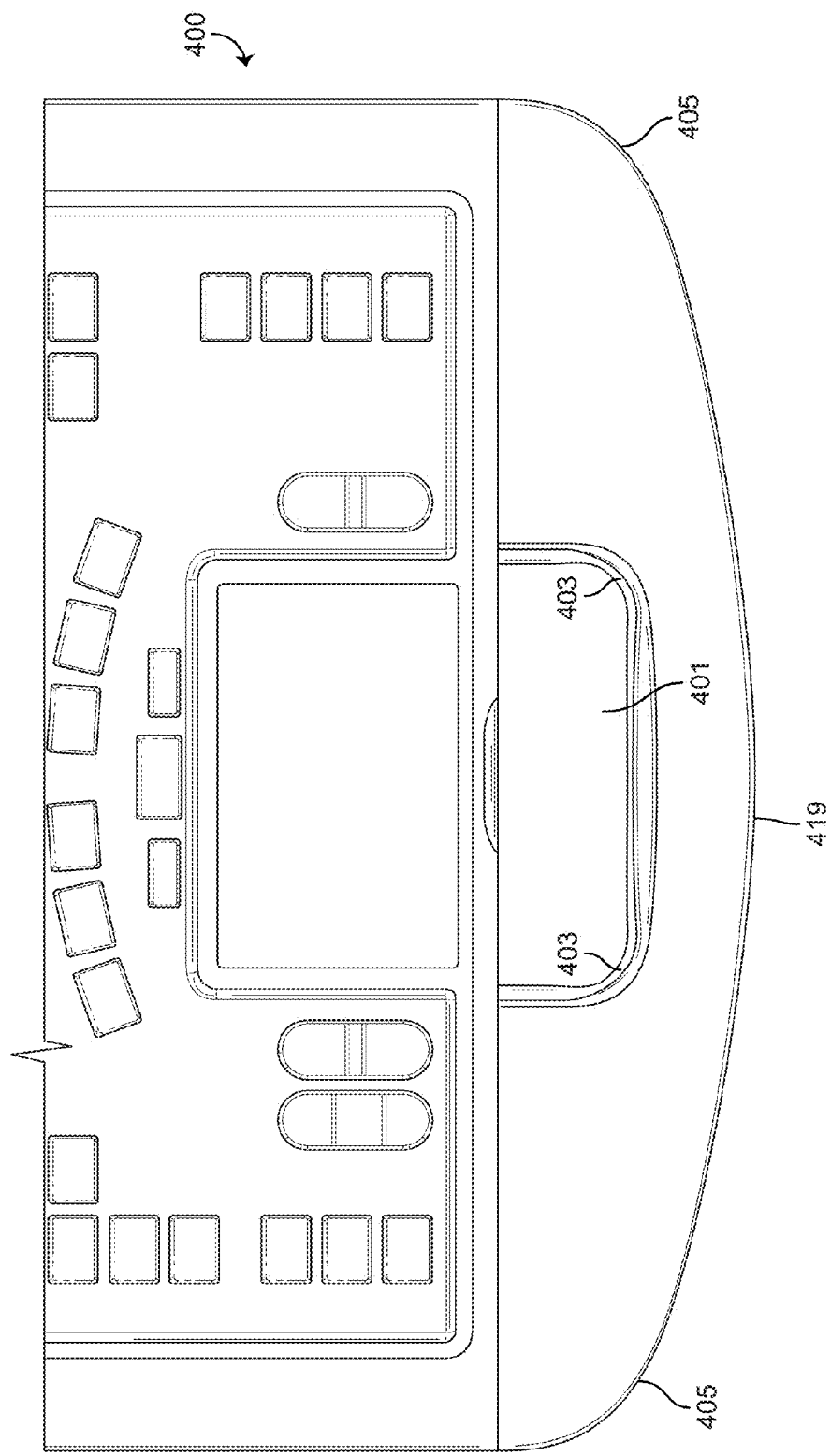
FIG. 10 illustrates a top view of an embodiment of the ergonomic handle system.

FIG. 10 illustrates a top view of ergonomic handle system 400 according to an exemplary embodiment. Front face 419 may be curved such that it extends outward from rounded corners 405. In some embodiments, handle cutout 401 may include rounded handle cutout corners 403. Handle cutout corners 403 may be rounded to provide a more comfortable grip to a user.

Figure 11:
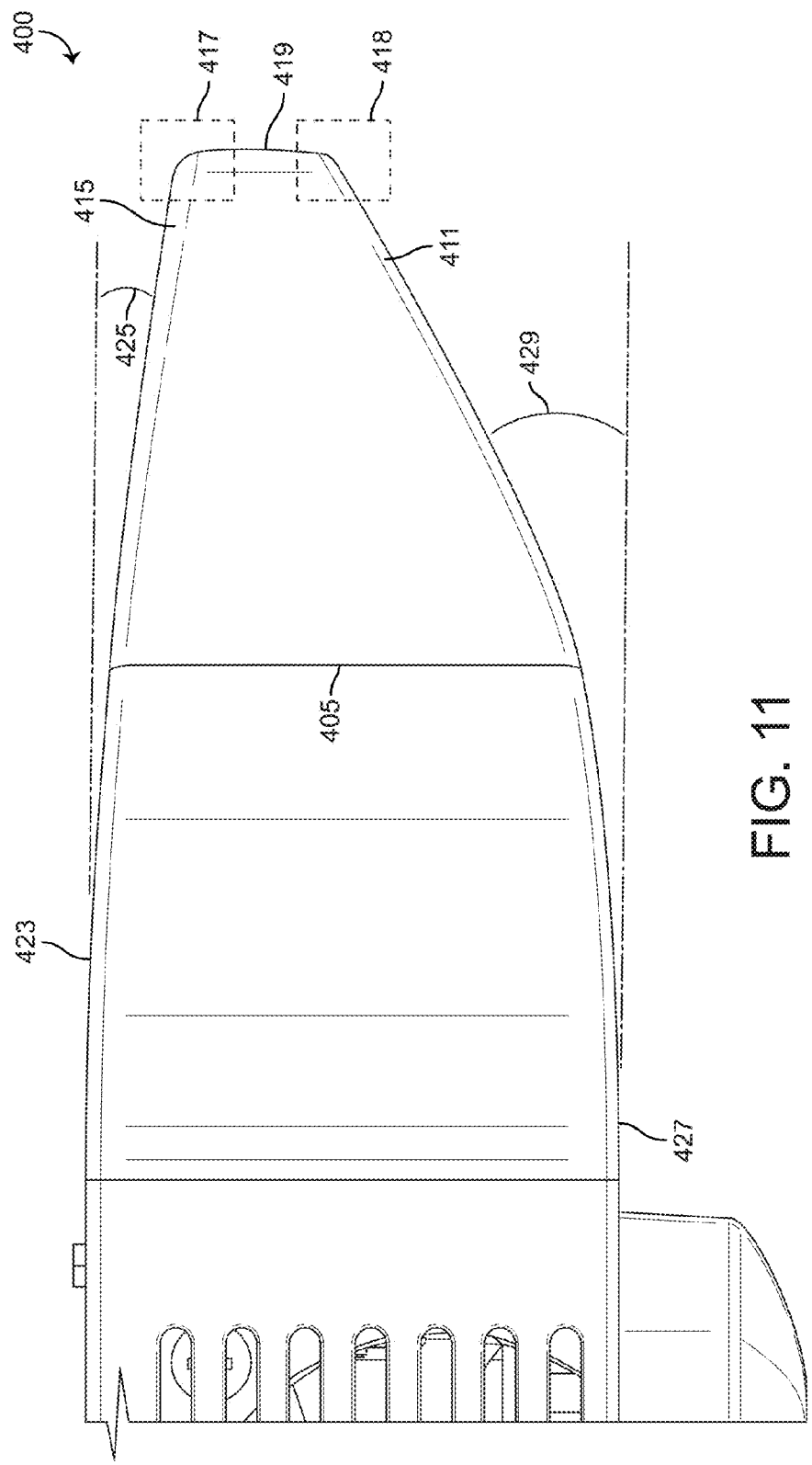
FIG. 11 illustrates a side view of an embodiment of the ergonomic handle system.

FIG. 11 illustrates a side view of ergonomic handle system 400 according to an exemplary embodiment. Rounded corner 405 is depicted extending from a portion of the portable ultrasound system 100 to front face 419. Upper face 423 may be angled at angle 425 to meet front face 419 at upper edge 415. In some embodiments, upper face 423 may be rounded to meet front face 419. The area 417 in which front face 419 and upper face 423 meet (e.g., through upper edge 415) may be rounded. In some embodiments, area 417 may be chamfered.

Lower face 427 may be angled at angle 429 to meet front face 419 at lower edge 415. In some embodiments, lower face 427 may be rounded to meet front face 419. The area 418 in which front face 419 and lower face 423 meet (e.g., through lower edge 415) may be rounded. In some embodiments, area 418 may be chamfered.

Figure 12:
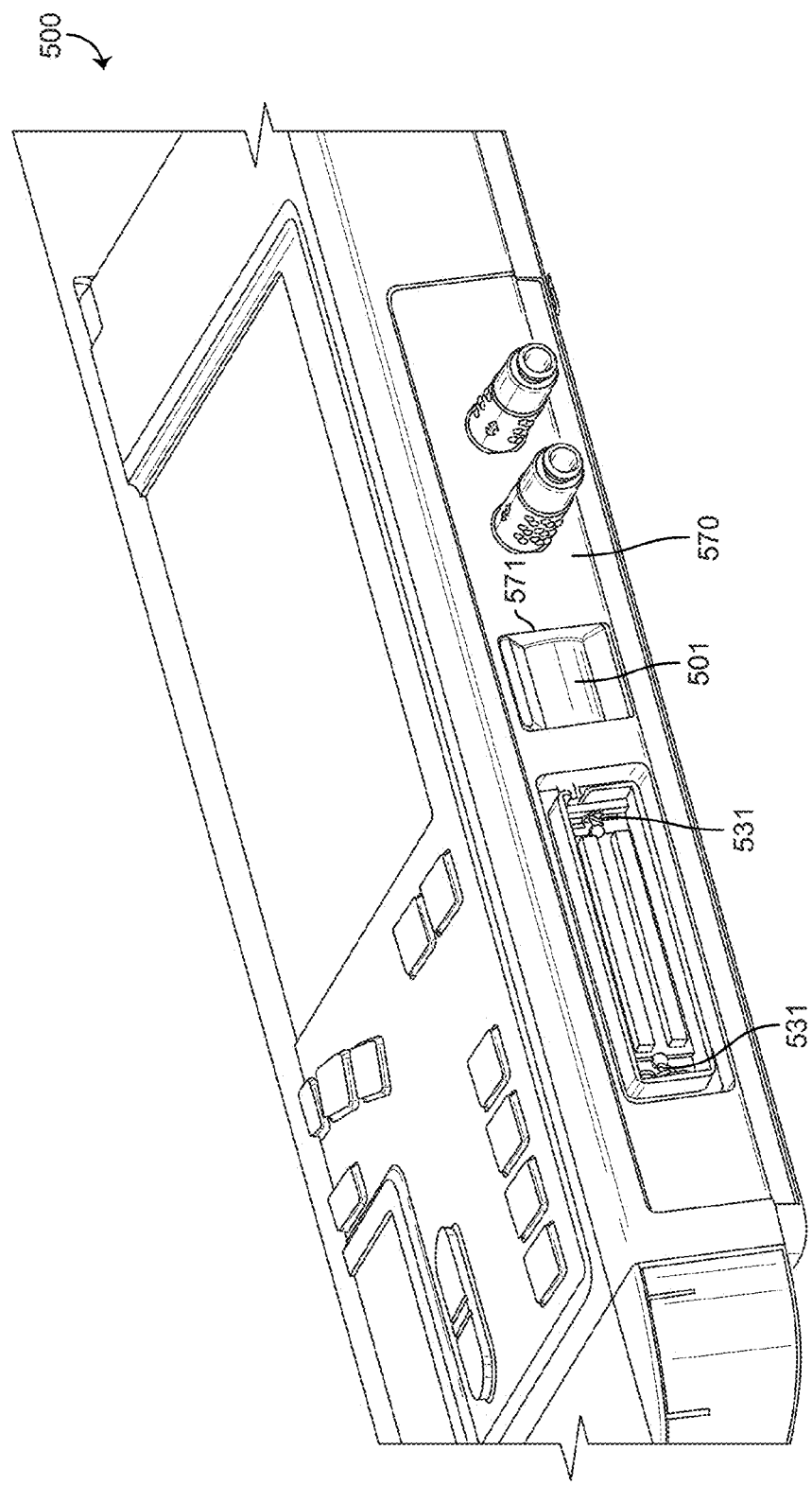
FIG. 12 illustrates an embodiment of the portable ultrasound device including a locking lever system of the invention.

FIG. 12 illustrates an exemplary embodiment of locking lever system 500. Generally, locking lever system 500 provides a mechanism which secures a transducer and/or ultrasound probe. Rotating a shaft connected to the locking lever moves insertion blades 531. Insertion blades 531 grasp a connector of the transducer and/or probe and pull it into place such that contacts within the transducer and/or probe are in secured contact with contacts within portable ultrasound system 100. With reference to FIG. 12 and FIG. 3A, locking lever system 500 locks ultrasound transducer/probe 187 into connection with transducer/probe pin interface 181.

Now with specific reference to FIG. 12, lever assembly 501 protrudes from side 570. This allows lever assembly 501 to be accessible to a user. Lever assembly 501 protrudes from side 570 through opening 571 in side 570. In some embodiments, side 570 is a side of main housing 150 and opening 571 is a cutout from main housing 150. In other embodiments, side 570 is an enclosure containing locking lever system 500, connectors for a transducer, and/or connectors for one or more ultrasound probes. The lever assembly 501 may protrude a small amount beyond side 570. This may provide easier access for a user's finger. Rotation of lever assembly 501 causes insertion blades 531 to rotate and to pull a connector into place and secure it.

Figure 13:
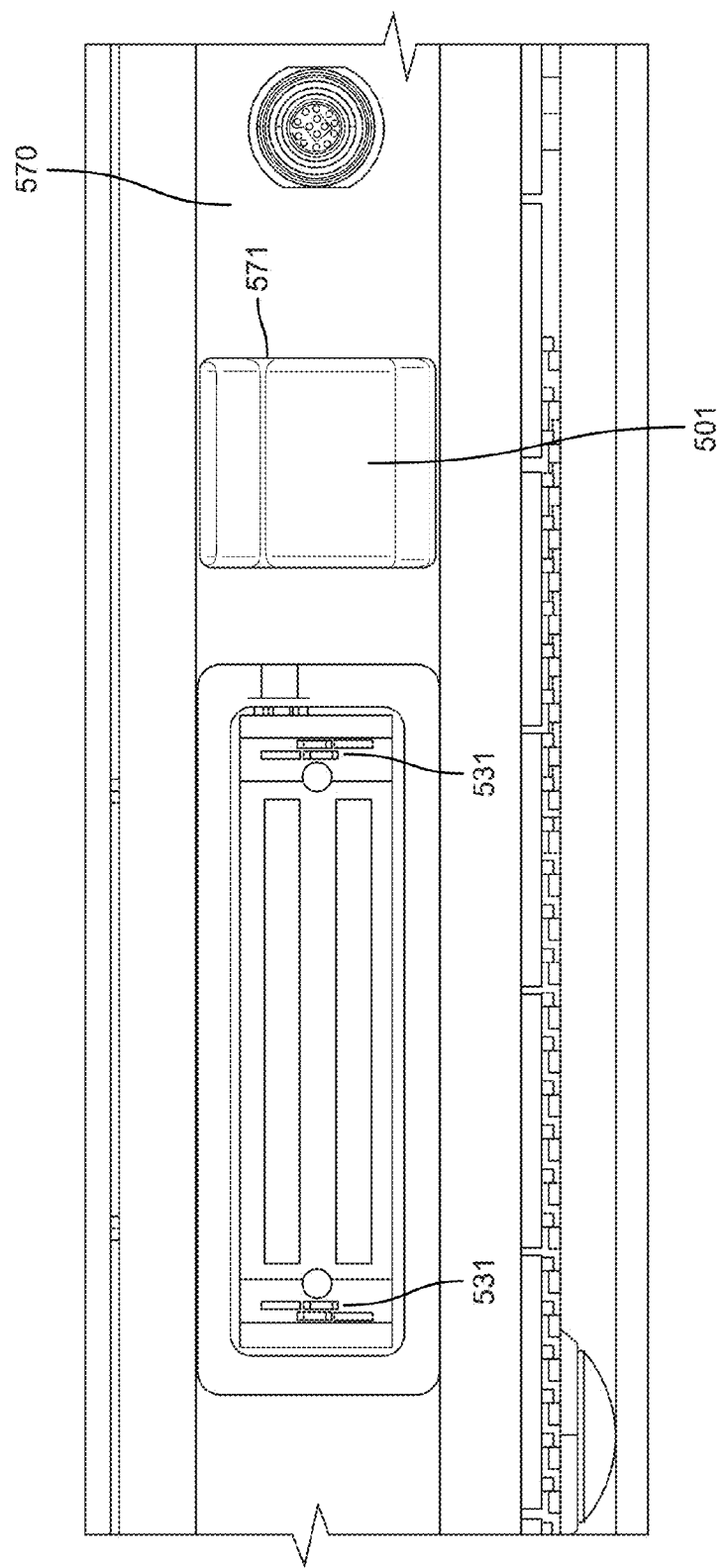
FIG. 13 illustrates a front view of an embodiment of a locking lever system according to one embodiment.

FIG. 13 illustrates a side view of an exemplary embodiment of locking lever system 500. Lever assembly 501 protrudes from side 570 through opening 571. A gap between lever assembly 501 and opening 571 may allow free rotation of lever assembly 501 relative to opening 571. Insertion blades 531 are depicted as two pairs of insertion blades. In some embodiments, other combinations of assertion blades 531 (e.g., one insertion blade per side) are used to pull in and secure a connector (e.g., a connector on an ultrasound probe or transducer).

Figure 14:
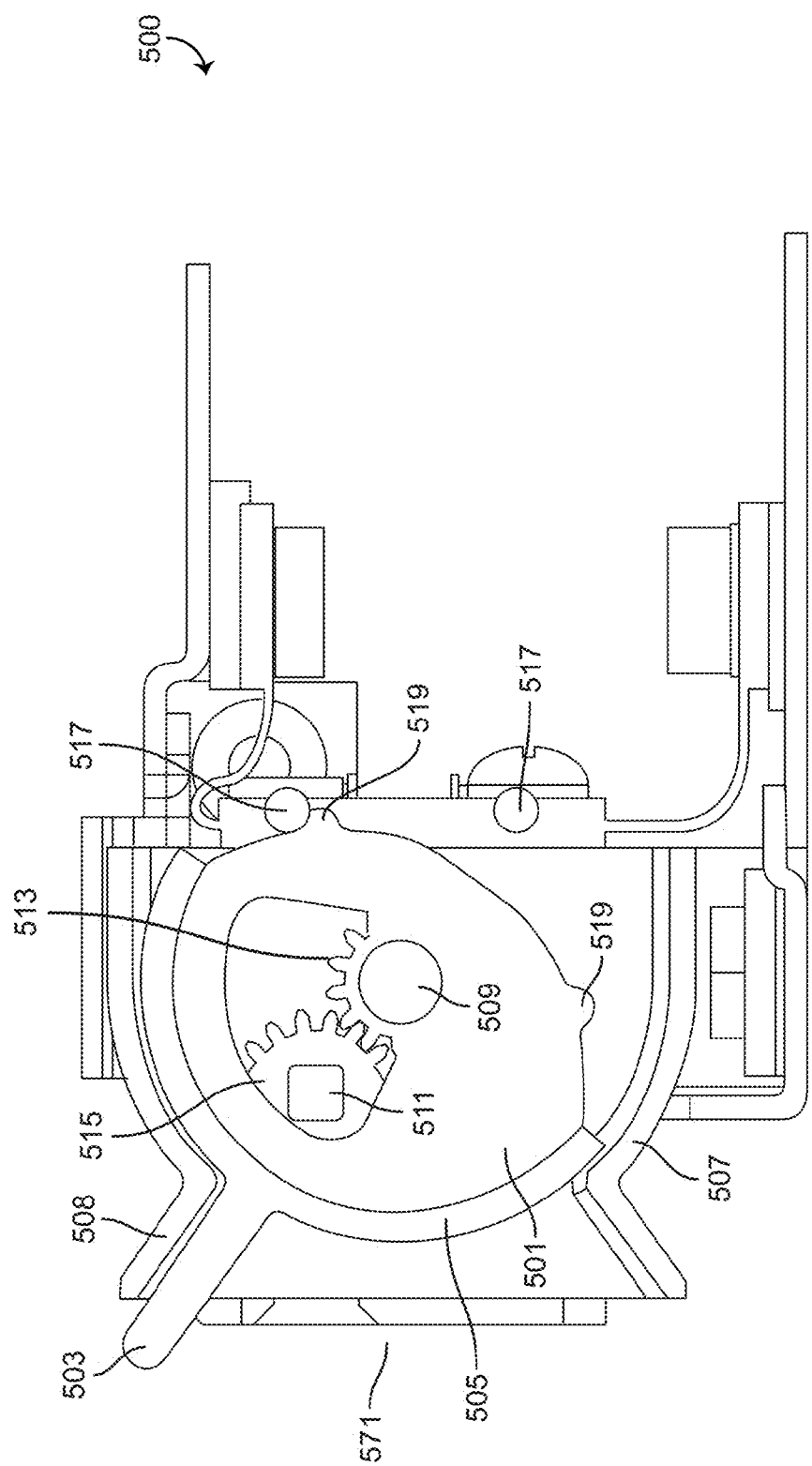
FIG. 14 illustrates a side cross section view of an embodiment of a locking lever system according to one embodiment.

FIG. 14 illustrates a cross section view of the side of locking lever system 500. In some embodiments, opening 571 may be defined by lever housing assembly 507. Lever housing assembly 507 may provide a sleeve in which lever assembly 501 rotates. Lever housing assembly 507 may also provide a flange 508 to prevent over rotation of lever assembly 501. In some embodiments, lever housing assembly 507 is formed as part of main housing 150 or side 570. In other embodiments, lever housing assembly 507 is attached to side 570. For example, lever housing assembly may be attached with fasteners, screws, nuts and bolts, adhesive, etc.

Lever assembly 501 rotates within lever housing assembly 507. In some embodiments, lever assembly 501 includes lever 503 and drum 505. Drum 505 may have a free running fit with lever housing assembly 507. In other embodiments, drum 505 may have a fit with lever housing assembly 507 which prevents or reduces inadvertent rotation of drum 505 (e.g., by providing friction or fit resistance to rotation). Drum 505 may transfer force from lever 503 to lever housing assembly 507. This may prevent excessive force on axel 509. Drum 505 may also keep lever 503 positioned relative to lever housing assembly 507. Drum 505 also includes a hole or bearing which allows lever assembly 501 to rotate about axel 509. In some embodiments, drum 505 includes an incorporated input gear 513. In other embodiments, drum 505 is coupled to input gear 513. The rotation of drum 505 due to a force on lever 503 causes input gear 513 to rotate. In some embodiments, axel 509 is fixed and drum 505 and input gear 513 rotate about axel 509. Axel 509 may be supported by lever assembly housing 507. In other embodiments, drum 505 and input gear 513 are fixed to axel 509 which rotates within an opening or bearing in lever assembly housing 507.

In some embodiments, drum 505, axel 509, and/or input gear 513 may be driven by an electric motor. In some embodiments, lever 503 may be replaced with a button (e.g., push button, capacitive sensor, ultrasound sensor, etc.) which when pushed or activated rotates drum 505, axel 509, and/or input gear 513 with an electric motor. Lever 503, drum 505, and/or opening 571 may be omitted in embodiments including an electric motor. In other embodiments, lever 503 is a switch which activates an electric motor to drive drum 505, axel 509, and/or input gear 513. In some embodiments, the electric motor may be a stepper motor, rotational solenoid, or solenoid configured to attach to a radius of drum 505 and impart a moment relative to axel 509.

Referring again to FIG. 14, drum 505 may include protrusions 519. Protrusions 519 may resist rotation of drum 505 by contacting pegs 517. This resistance may prevent unintentional locking or unlocking of locking lever system 500. The fit of drum 505 within lever assembly housing 507 may provide for contact between protrusions 519 and pegs 517 and also allow for protrusions 519 to rotate past pegs 517 when sufficient force is applied. In other embodiments, pegs 517 and/or protrusions 519 are made of a material which plastically deforms given sufficient force. This allows drum 505 to rotate and protrusions 519 to pass pegs 517.

Rotation of input gear 513 drives output gear 515. Output gear 515 is coupled to output shaft 511. In some embodiments, drum 505 is hollow or partially hollow such that output gear 515 is within drum 505. Output shaft 511 may also partially extend within drum 505. Positioning output gear 515 and output shaft 511 off axis to axel 509 and parallel with axel 509 allows lever assembly 501 to rotate about a point centered along the height of side 570. By sizing and/or positioning input gear 513 and output gear 515, lever assembly 501 may be centrally located in lever assembly housing 507. Input gear 513 and output gear 515 may form a counter rotating pair. As drum 505 rotates clockwise due to force applied to lever 503, output shaft 511 rotates counter clockwise. Similarly, as drum 505 rotates counterclockwise due to force applied to lever 503, output shaft 511 rotates clockwise.

Figure 15:
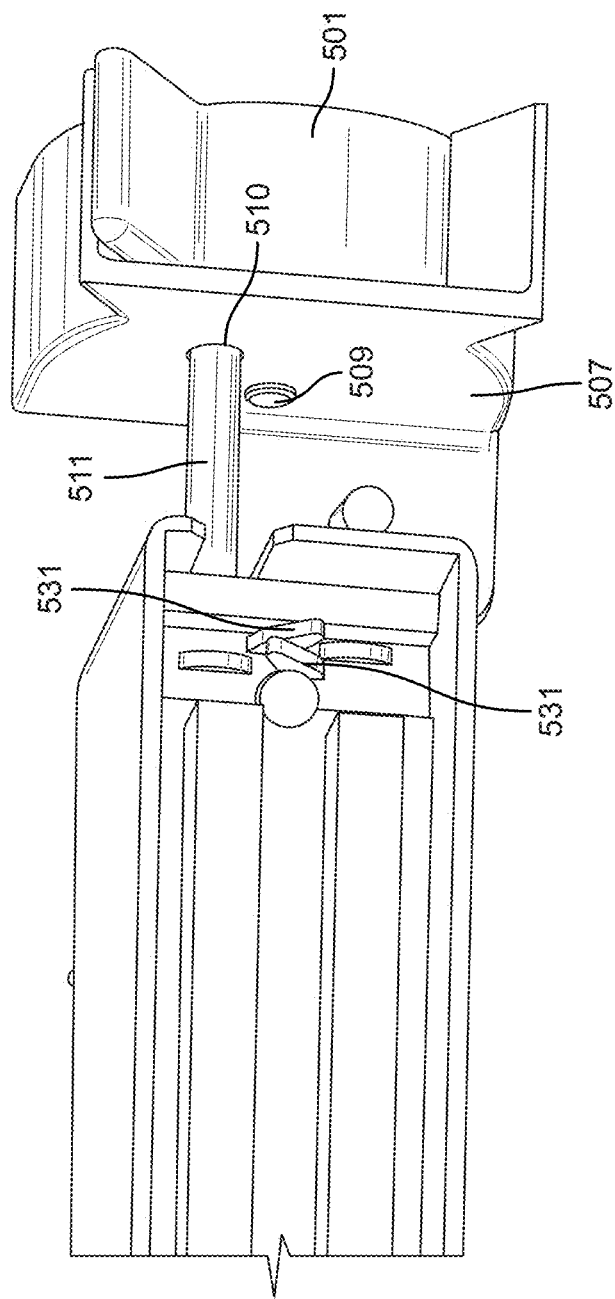
FIG. 15 illustrates a view of components of an embodiment of a locking lever system according to one embodiment.

FIG. 15 illustrates a front view of one embodiment of locking lever system 500 without side 570 pictured. Lever assembly 501 fits within lever assembly housing 507. Axel 509 is shown supported by lever assembly housing 507. In some embodiments, axel 507 may be prevented from sliding out of lever assembly housing 507 by a washer and/or clip. Lever assembly housing 507 also includes an opening 510 which allows output shaft 511 to exit lever assembly housing 507. In some embodiments, opening 510 may include a bearing. In some embodiments, opening 510 in lever housing assembly 507 may help to position and/or support output shaft 511 and/or output gear 515 (i.e. output gear 515 may be fixed to output shaft 511). Output shaft 511 drives insertion blades 531. In some embodiments, insertion blades 531 are rotated by output shaft 511. Insertion blades 531 may extend outward from output shaft 511 or another axis of rotation. This may allow a portion of insertion blade 531 to contact a connector, apply torque to the connector, and pull the connector in towards portable ultrasound system 100.

In some embodiments, insertion blades 531 are connected directly to output shaft 511. In other embodiments, one insertion blade 531 of a pair of insertion blades 531 may be connected directly to output shaft 511. The other insertion blade 531 may be connected to output shaft 511 through a gear. The gear may allow the second insertion blade 531 to rotate about an axis offset from and parallel to the axis of rotation for the first insertion blade 531. The gear may also allow the second insertion blade to counter rotate in relation to the first insertion blade. In other embodiments, both insertion blades 531 of a pair of insertion blades 531 are connected to output shaft 511 through one or more gears, cams, levers, etc.

Figure 16A:
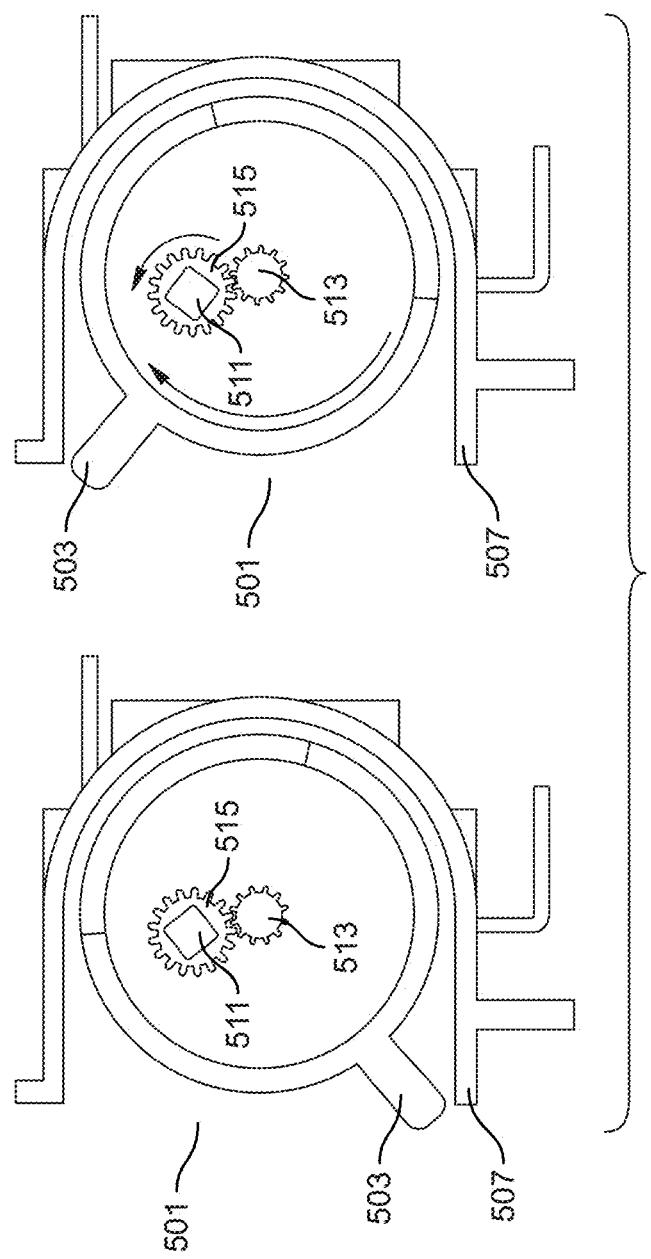
FIG. 16A illustrates the operation of an embodiment of a locking lever system according to one embodiment.

FIG. 16A illustrates an embodiment of locking lever system 500 in locked and unlocked positions. When lever 503 is down, lever assembly 501 is in lock position. In lock position, insertion blades 531 have rotated and moved to pull the connector of an ultrasound probe or transducer into contact with a connector of portable ultrasound system 100. Lever assembly 501 may be held in lock position by protrusion 519 and peg 517 as explained with reference to FIG. 13. Lock position may be defined by peg 517, protrusion 519 and/or lever assembly housing 507. In some embodiments, lock position is defined by when lever assembly 501 has rotated counterclockwise, or toward the bottom of portable ultrasound system 100, such that lever assembly housing 507 does not allow for further rotation of lever assembly 501 (e.g., lever assembly 501 cannot rotate any further, not including slight movement due to fit with lever assembly housing 507, because it is stopped from rotating by lever assembly housing 507).

Similarly, when lever 503 is up, lever assembly 501 is in unlock position. In unlock position, insertion blades 531 have rotated and moved to release the connector of an ultrasound probe or transducer. Lever assembly 501 may be held in unlock position by protrusion 519 and peg 517 as explained with reference to FIG. 13. Unlock position may be defined by peg 517, protrusion 519 and/or lever assembly housing 507. In some embodiments, lock position is defined by when lever assembly 501 has rotated clockwise, or toward the top of portable ultrasound system 100, such that lever assembly housing 507 does not allow for further rotation of lever assembly 501 (e.g., lever assembly 501 cannot rotate any further, not including slight movement due to fit with lever assembly housing 507, because it is stopped from rotating by lever assembly housing 507). In some embodiments, the downward locking position and upward unlocking position are a result of counter rotating gears input gear 513 and output gear 515.

As described, locking lever system 500 locks in the downward position and unlocks in the upward position. This enhances the usability of portable ultrasound system 100 as a downward lock position and upward unlock position is more intuitive to a user. Locking lever system 500 also increases the durability of portable ultrasound system 100 by applying a mechanical advantage to secure ultrasound probes/transducers. This reduces the amount of force a user must apply to lock and unlock an ultrasound transducer/probe.

In some embodiments, when lever 503 is up, lever assembly 501 is in lock position, and when lever 503 is down, lever assembly 501 is in unlock position. This configuration may be achieved by eliminating input gear 513 and output gear 515. In such a case, lever assembly 501 may directly drive output shaft 511 (e.g., lever assembly 501 is coupled to output shaft 511 and causes it to rotate when moved). In other embodiments, the connection between insertion blades 531 (e.g., directly connected to output shaft 511, cams, gears, etc.) may be configured to engage insertion blades 531 when lever 503 is up and disengage insertion blades 531 when lever 503 is down.

With continued reference to FIG. 16A, input gear 513 and output gear 515 may provide gearing with a variety of gear ratios. In the depicted embodiment, output gear 515 and input gear 513 are sized so as to provide a mechanical advantage to inputs through lever 503. Input gear 513 and output gear 515 may be sized such that the torque ratio is greater than one. This reduces the amount of force that a user is required to input through lever 503 in order to engage or disengage insertion blades 513. For example, the gear ratio of input gear 513 to output gear 515 may be 1:1.33 (e.g., input gear 513 rotates through 1.33 revolutions for every rotation of output gear 515). In one embodiment, input gear 513 rotates 80 degrees from one position to another, and output gear 515 rotates 60 degrees from one position to another. In other embodiments, different gear ratios are used. The gear ratio may be selected to change the mechanical advantage, change the position of output shaft 511 relative to input gear 513, etc. In some embodiments, the mechanical advantage of locking lever system 500 is increased by using a longer lever 503. Lever assembly housing 507 and lever 503 may be configured to allow lever 503 to move through the entire range of the housing. This provides a greater rotation of input gear 513 which in turn allows input gear 513 and output gear 515 to be sized for greater mechanical advantage while still providing enough rotation to engage and disengage insertion blades 513. For example, lever assembly housing 507 may be configured to allow lever 503 to rotate through 80 degrees. In other embodiments, lever housing assembly 507 is configured to allow for greater or lesser rotation of lever 503.

Figure 16B:
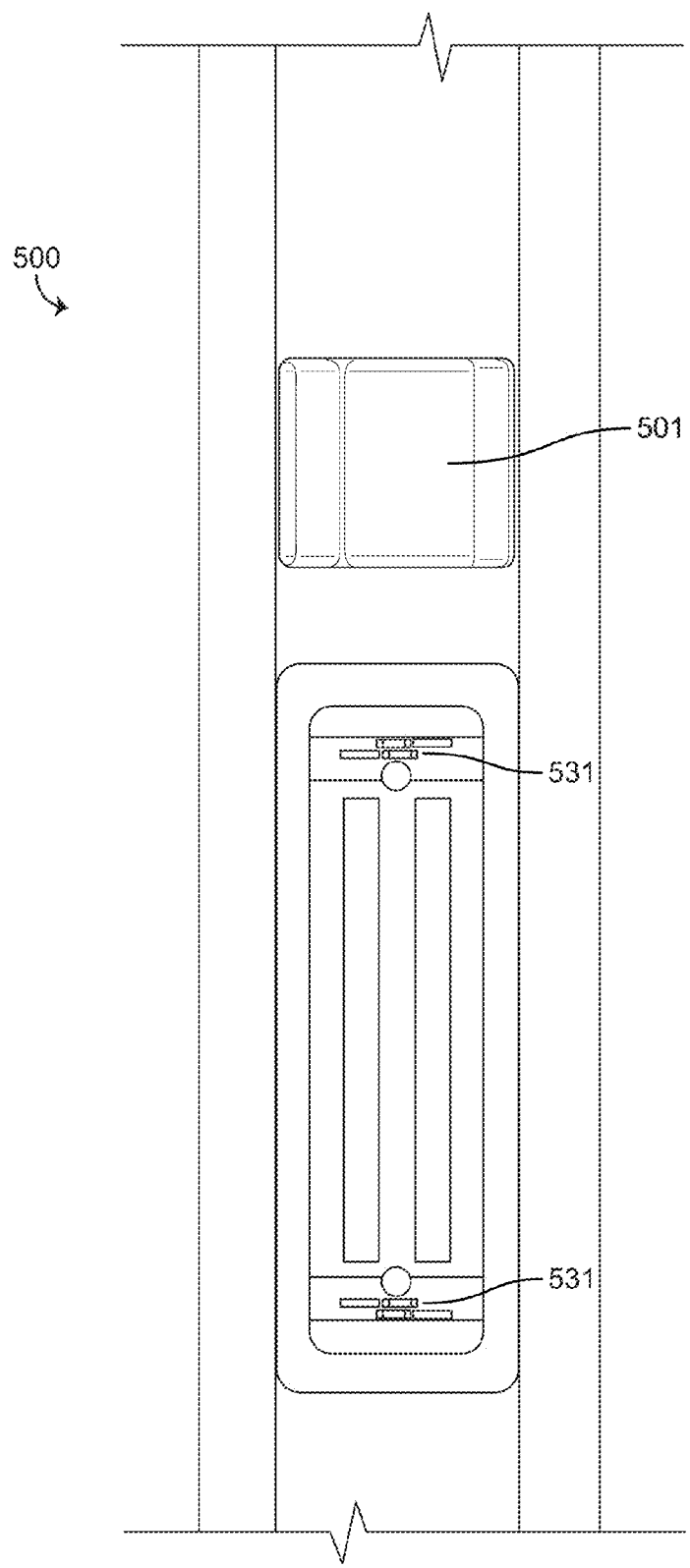
FIG. 16B illustrates a vertically oriented locking level system according to one embodiment.

Referring now to FIG. 16B, locking lever system 500 is illustrated in a vertical configuration according to one embodiment. In some embodiments of portable ultrasound system 100, locking lever system 500 is oriented vertically.

Lever assembly 501 rotates in a horizontal plane (e.g., the axis of rotation runs vertically). Advantageously, orienting locking lever system 500 vertically allows for different packaging of portable ultrasound system 100. For example, portable ultrasound system 100 may be a cart based system or included in a portable cart. Vertical orientation may allow for the inclusion of a greater number of features and/or connections.

Figure 16C:
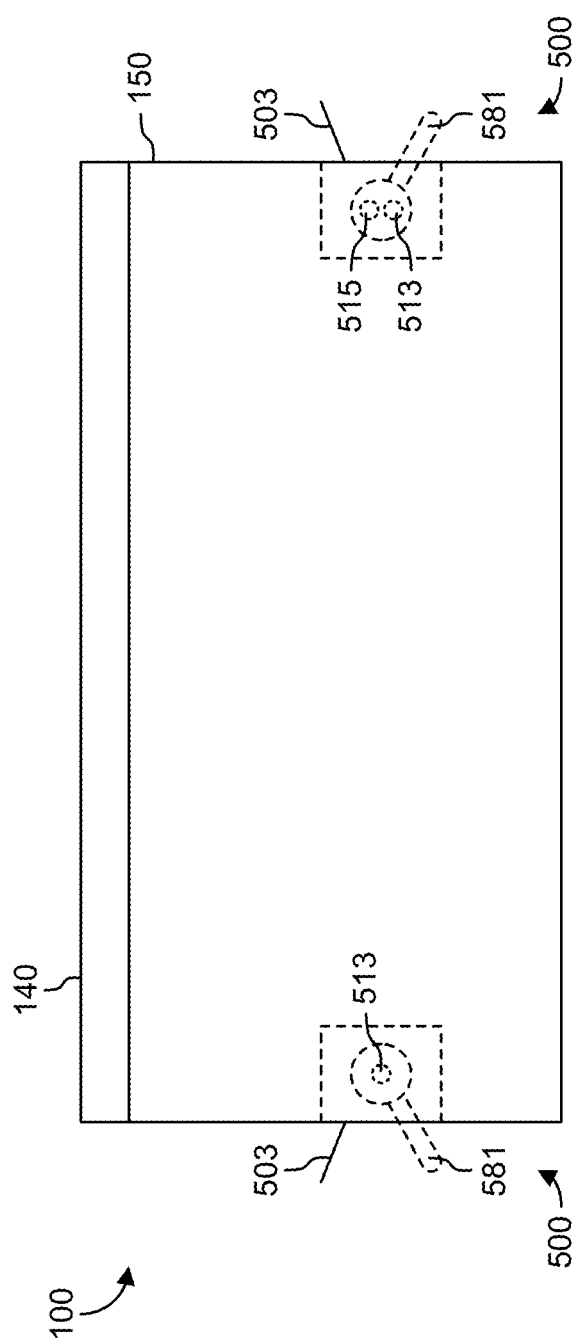
FIG. 16C illustrates a portable ultrasound system having a conventional locking lever system and a locking lever system with counter rotating gears according to one embodiment.

Referring now to FIG. 16C, a top down view of portable ultrasound system 100 is illustrated according to one embodiment. Portable ultrasound system 100 can include vertically oriented locking lever systems 500 on the right and left hand sides. In alternative embodiments, a cart removably coupled to portable ultrasound system 100 can include vertically oriented locking lever systems 500. Advantageously, the vertical orientation of locking lever system 500 may increase the number of ultrasound transducers/probes which can be connected to portable ultrasound system 100. In one embodiment, portable ultrasound system 100 includes one vertically oriented locking lever system 500 which includes counter rotating gears (e.g., input gear 513 and output gear 515). The locking lever system 500 may have counter rotating gears as previously described in greater herein with reference to FIGS. 14 and 16A. This locking lever system 500 can be located on one side of portable ultrasound system 100 (e.g., the right side as illustrated in FIG. 16C). Portable ultrasound system 100 can further include a second vertically oriented locking lever system 500 located on the opposite side (e.g., left side as illustrated in FIG. 16C). The second locking lever system 500 does not include counter rotating gears. The second locking lever system instead is directly driven by lever 503 or includes a third gear in the gear train connecting lever 503 to output shaft 511 (not pictured). Advantageously, this configuration maintains a consistent use model with the lock and unlock positions of levers 503 being consistent on each side of portable ultrasound system 100. For example, locking lever system 500 can be in unlock position when levers 503 are positioned towards display housing 140 (e.g., away from a user). Locking lever system can be locked when levers 503 are positioned away from display housing 140 as indicated by dashed lines 581.

Referring now to FIG. 16D, a schematic front view of portable ultrasound system 100 including cart base 583 having two locking lever systems 500 is illustrated according to one embodiment. Locking lever systems 500 can be horizontally oriented with one or more locking lever systems 500 on each side of portable ultrasound system 100. Portable ultrasound system 100 can connect to cart base 583. Cart base 583 is a base which includes a stand and wheels. This allows for portable ultrasound system 100 to be portable and positioned at a convenient height for use by a user. Additionally, cart base 583 can include additional connections for ultrasound probes/transducers, storage for ultrasound probes/transducers, an electrical power source for portable ultrasound system 100 (e.g., an additional battery), and/or other hardware which supports portable ultrasound system 100.

In one embodiment, cart base 583 includes one horizontally oriented locking lever system 500 which includes counter rotating gears (e.g., input gear 513 and output gear 515). The locking lever system 500 may have counter rotating gears as previously described in greater herein with reference to FIGS. 14 and 16A. This locking lever system 500 can be located on one side of portable ultrasound system 100 (e.g., the right side as illustrated in FIG. 16D). Portable ultrasound system 100 can further include a second horizontally oriented locking lever system 500 located on the opposite side (e.g., left side as illustrated in FIG. 16D). The second locking lever system 500 does not include counter rotating gears. The second locking lever system instead is directly driven by lever 503 or includes a third gear in the gear train connecting lever 503 to output shaft 511 (not pictured). Advantageously, this configuration maintains a consistent use model with the lock and unlock positions of levers 503 being consistent on each side of portable ultrasound system 100. For example, locking lever system 500 can be in unlock position when levers 503 are positioned upwards towards display housing 140 (e.g., away from a user). Locking lever system can be locked when levers 503 are positioned downwards and away from display housing 140 as indicated by dashed lines 581.

When rotating lever 503 of the left hand locking lever system 500 upward, the input received is in the clockwise direction. Conversely, when rotating lever 503 of the right hand locking lever system 500 upward, the input received is in the counterclockwise direction. Therefore, one locking lever system 500 has counter rotating gears (e.g., input gear 513 and output gear 515) to rectify the inputs from levers 503. The left hand locking lever system is directly driven by lever 503 (e.g., counter rotating gears are not used). Therefore, an upward force on lever 503 provides a clockwise input which moves locking lever system 500 into the unlocked position. The right hand locking lever system includes input gear 513 and output gear 515. Therefore, an upward force on lever 503 provides a counterclockwise input to input gear 513 which drives output gear 515 in a clockwise direction which in turn moves locking lever system 500 into the unlocked position. Advantageously, the lock positions (e.g., down) and unlock positions (e.g., up) of levers 503 are consistent for both locking lever systems 500.

In further embodiments, the locked and unlocked positions can differ (e.g., locking lever systems 500 can be in the locked position when levers 503 are up). In still further embodiments, a left hand and right hand locking lever system 500 can be included in portable ultrasound system 100 rather than cart base 583. This provides the same advantages discussed herein directly to portable ultrasound system 100.

FIG. 17 illustrates an embodiment of status indicator system 600. Status indicator system 600 provides information to a user of portable ultrasound system 100. For example, portable ultrasound system 100 may run on battery power. A user therefore may want to check the battery status especially if the system is being used in an area without ready access to a recharging source. Status indicator system 600 allows a user to check the battery power level quickly and easily. In some embodiments, status indicator system 600 includes one or more indicator light emitting diodes ("indicator LED") 603. Status indicator system 600 may also include power light emitting diode ("power LED") 601. Information may be displayed to a user following activation of proximity sensor 605. In the illustrated embodiment, indicator LEDs 603, power LED 601, and proximity sensor 605 are included within enclosure 607.

In embodiments, enclosure 607 is a recessed area. Enclosure 607 may, as illustrated, be located partially within handle cutout 401 on the side opposite handle 407. The concave area of enclosure 607 may extend from within handle cutout 401 onto main housing 150. This location may provide for easy access to proximity sensor 605 and reduce distraction to a user during an examination procedure. FIG. 17 illustrates an embodiment of enclosure 607 wherein enclosure 607 is a hemispherical like concave structure which is recessed from handle cutout 401 and extends onto main housing 150. This may also be seen in the embodiment illustrated in FIG. 18. Still referring to FIG. 17, enclosure 607 can be a recessed section shaped as a quarter cylinder with tapered or hemispherical like ends. Enclosure 607 can include a recessed area having a variety of shapes in various embodiments. The recessed structure of some embodiments of enclosure 607 allows a user to locate enclosure 607 by feel. This in turn allows a user to easily locate enclosure 607, for the purpose of checking system status, in cases where visual location may be difficult (e.g., low light or darkness makes seeing status indicator system 600 difficult). In other embodiments, enclosure 607 may be located in other areas near handle 407. In further embodiments, enclosure 607 may be located elsewhere on portable ultrasound system 100. For example, enclosure 607 may be located in one or more of the top cover of display housing 140, display housing 140 above main screen 130, a side of main housing 150, etc.

In alternative embodiments, enclosure 907 is a raised (e.g., convex) dome or semi-dome. This may assist a user in locating enclosure 607 and/or proximity sensor 605 by touch. Advantageously, this allows a user to easily check a status of by triggering status indicator system 600 via proximity sensor 605.

Although the depicted embodiment illustrates indicator LEDs 603, power LED 601, and proximity sensor 605 as within enclosure 607, some components may be located in other areas. For example, enclosure 607 may include only proximity sensor 607. This may allow for location of proximity sensor 607 by touch. Indicator LEDs 603 and/or power LED 601 may be located in other locations. For example, indicator LEDs 603 and/or power LED 601 may be located in one or more of the top cover of display housing 140, display housing 140 above main screen 130, a side of main housing 150, etc.

In other embodiments, enclosure 607 is recessed into handle cutout 401 and/or main housing 150. For example, enclosure 607 may be a concave dome or semi-dome. The recessed geometry of enclosure 607 may act as a tactile cue allowing a user to locate proximity sensor 605 by feel in order to check the system status. In further embodiments, enclosure 607 may be flush with handle cutout 401 and/or main housing 150. Haptic feedback may be provided (e.g., by a vibration motor) to assist a user in locating proximity sensor 605.

Figure 18:
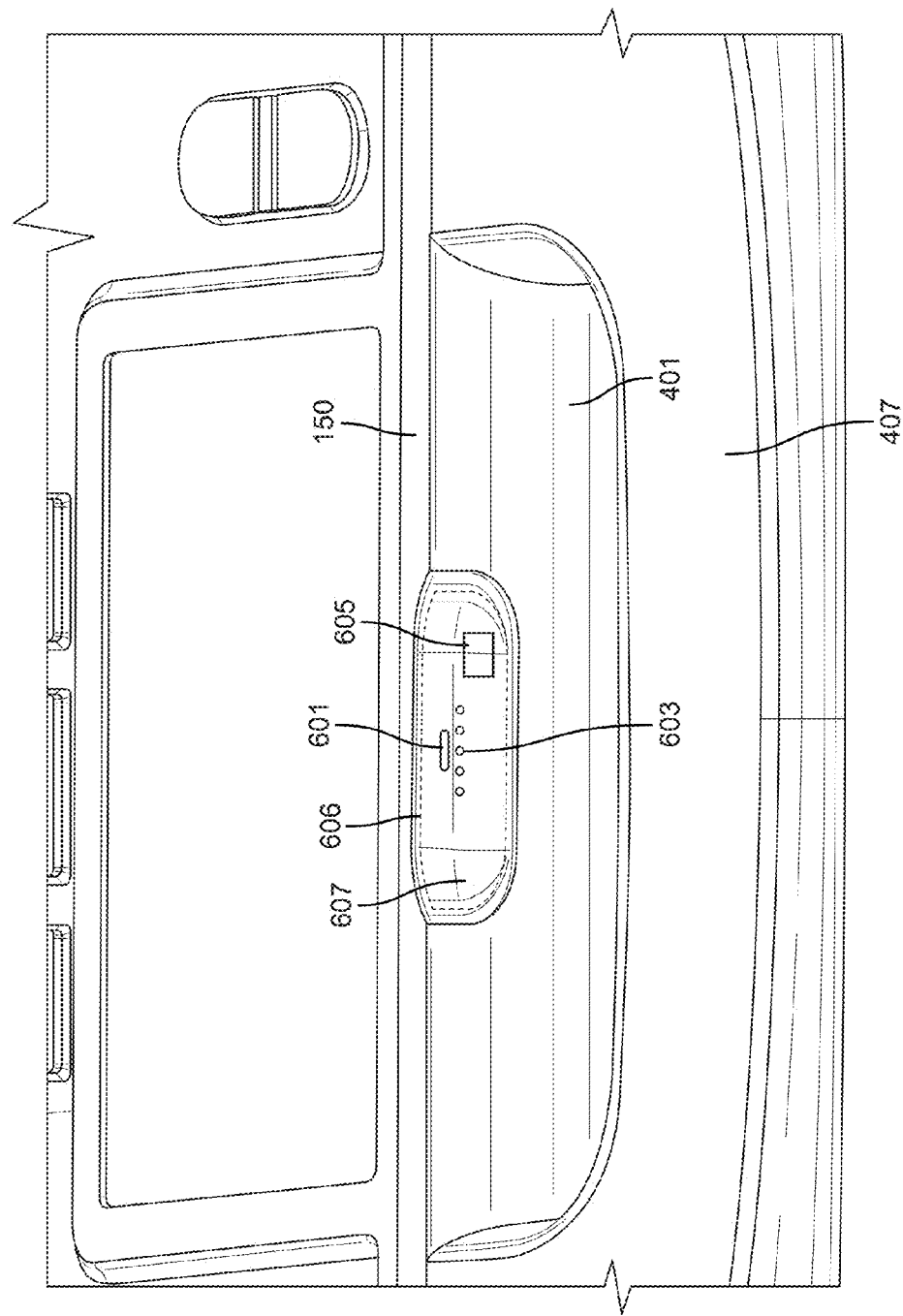
FIG. 18 illustrates an embodiment of a status indicator system for providing information to a user when triggered by a proximity sensor.

Referring now to FIG. 18, the position of proximity sensor 605 is shown according to one embodiment. Proximity sensor 605 may be located in enclosure 607. In such a case, proximity sensor 605 may be configured to detect and be activated by a user which touches enclosure 607. This allows a user to find enclosure 607 by touch and simultaneously activate proximity sensor 605. Proximity sensor(s) 605 may be located variously within region 606 in various alternative embodiments. In other embodiments, proximity sensor 605 is located remote from enclosure 607. Enclosure 607 may function solely as a visual cue for indicator LEDs 603 and/or power LED 601. In further embodiments, proximity sensor 605 may be located in areas a user is likely to touch as there is no visual cue for activating status indicator system 600. For example, proximity sensor 605 may be located in handle 407, touchscreen 110, and/or touchscreen 120. In further embodiments, multiple proximity sensors 605 are used. For example, multiple proximity sensors 605 may be located in different locations on portable ultrasound device 100. Multiple proximity sensors 605 may also be located in substantially the same area in order to ensure a user input intended to cause display of the system status activates as least one proximity sensor 605.

In further embodiments, proximity sensor(s) 605 are located such that they are triggered when display housing 140 is opened from a closed to open position. For example, proximity sensor(s) 605 can be located in display housing 140 near an area or areas likely to be used by a user when opening display housing 140. Proximity sensor(s) 605 can be located along one or more edges of display housing 140 such that a user's hand is detected when a user opens display housing 140. In further embodiments, proximity sensor 605 is located in region 606 such that a user will trigger proximity sensor 605 when opening the lid of portable ultrasound system 100. For example, region 606 and/or enclosure 607 may be a recessed area in which a user places one or more fingers to grip the lid of portable ultrasound system 100 while opening the lid.

Status indicator system 600 can be a system or subsystem of portable ultrasound system 100 which remains on while portable ultrasound system 100 is off, in low powered mode, or otherwise not in use. Status indicator system 600 can draw power from one or more power sources available to portable ultrasound system 100 to remain powered while portable ultrasound system 100 is off, in a sleep mode, in a hibernation mode, in a low power mode, or otherwise not in use. For example, status indicator system 600 may draw power from one or more batteries. Advantageously, this allows a user to check the status of portable ultrasound system 100 without turning on portable ultrasound system 100 or otherwise exiting a low power or off mode. For example, a user may check the charge level of one or more batteries of portable ultrasound system 100 without booting up, turning on, exiting a sleep mode, exiting a hibernation mode, or otherwise altering the operating state of portable ultrasound system 100.

In alternative embodiments, proximity sensor 605 detects the proximity of display housing 140 when display housing 140 is in a closed position. For example, proximity sensor 605 can be located within main housing 150 and be configured to detect display housing 140 when in a closed position. Status indicator system 600 can be configured to display a status using indicator LEDs 603 and/or power LED 601 when display housing 140 is not detected by proximity sensor 605. Status indicator system 600 may be further configured to cease display of a status and turn off indicator LEDs 603 and/or power LED 601 after a predetermined amount of time. For example, status indicator system 600 may detect that display housing 140 is no longer triggering proximity sensor 605 and being to display a status, and following 5 seconds, status indicator system may cease displaying the status. Upon renewed detection of display housing 140 by proximity sensor 605, status indicator system can repeat the same cycle.

In some embodiments, proximity sensor 605 is a capacitive sensor. Proximity sensor 605 may project an electromagnetic field and read changes in capacitance due to an object entering the field. For example, proximity sensor 605 may project an electromagnetic field beyond enclosure 607 to detect a user's finger or hand coming near or into contact with enclosure 607. In embodiments where proximity sensor 605 is a projected capacitance sensor, proximity sensor 605 may be located entirely in enclosure 607. Furthermore, a window in enclosure 607 or other feature providing a line of site to proximity sensor 605 may not be necessary. Proximity sensor 605 may detect a user without a line of sight to the user. In other embodiments, proximity sensor 605 may be a resistive touch sensor. In such embodiments, proximity sensor 605 may be a resistive touch sensor which is activated by a user's touch anywhere on enclosure 607. A resistive touch sensor may also allow proximity sensor 605 to function accurately when a user is wearing a glove (e.g., rubber glove, latex glove, etc.). In further embodiments, proximity sensor 605 may be one or more of an infrared sensor, ultrasound sensor, laser rangefinder, sonar, photocell, optical sensor, etc. In some embodiments, enclosure 607 may have a window (e.g., glass section) or other feature to facilitate operation of proximity sensor 605.

Indicator LEDs 603 are activated when proximity sensor 605 is activated (e.g., when an object is detected). In some embodiments, this occurs when a user touches the recessed surface defined by handle cutout 401 (e.g., handle area). The user requests that information be displayed via indicator LEDs 603 and/or power LED 601 by activating proximity sensor 605. The illumination of one or more of indicator LEDs 603 and power LED 601 may signal to a user that information about the system status is being displayed. In some embodiments, haptic feedback may also be provided to indicate to a user that proximity sensor 605 has been activated (e.g., triggered by detection of an object). Indicator LEDs 603 may include one or more LEDs. These LEDs may be configured to display various information regarding system status. For example, indicator LEDs 603 may display information regarding remaining battery power, remaining time to complete charge of a battery, available/remaining memory for storage of examination results, strength of wireless network connection (e.g., WiFi, Zigbee, Bluetooth, a cellular connection, etc.), if a wireless connection is established, etc. Power LED 601 may display information regarding whether portable ultrasound system 100 is on or off, whether computational resources are being used, that portable ultrasound system 100 is in a power saving mode, etc.

In some embodiments, indicator LEDs 603 display information by sequentially illuminating a set of indicator LEDs 603 out of the total number available. For example, five of five indicator LEDs 603 may be illuminated to indicate a full strength network connection, four of five indicator LEDs 603 may be illuminated for a near full strength network connection, etc. In other embodiments, indicator LEDs 603 may be illuminated with different colors. Indicator LEDs 603 may be illuminated in different colors corresponding to different information to be displayed. For example, indictor LEDs 603 may illuminate green to correspond to a majority of batter power remaining, yellow to correspond to less than half of battery power remaining, and red for battery power near depleted. In some embodiments, a series of indicator LEDs 603 may be illuminated with different colors. For example, a first LED may be red. A second, third, and fourth LED may be yellow. And a fifth LED may be green. Indicator LEDs 603 may be LEDs configured to emit light of a certain color, LEDs with dyed domes, and/or LEDs configured to selectably emit one of a variety of colors. In further embodiments, indicator LEDs 603 may display information by the frequency with which they are illuminated and turned off. For example, a solid red indicator LED 603 may indicate that ten percent of battery power remains while a flashing red indicator LED 603 may indicate that five percent of battery power remains. In additional embodiments, the brightness of indicator LEDs 603 are adjusted to convey information to a user. For example, a bright green indicator LED 603 may indicate that ninety or more percent of battery power remains. A duller/dimmer green indicator LED 603 may indicate that eighty percent to ninety percent of batter power remains. These same information display techniques may be used to display information with power LED 601. For example, power LED 601 may be illuminated green to indicate that portable ultrasound system 100 is on, yellow to indicate the system is in a standby mode, and red to indicate the system is turned off.

One or more of these information display techniques (sequential illumination, selective use of color, flashing illumination, brightness of illumination, etc.) may be combined in a single embodiment of status indicator system 600. For example, the color of indicator LEDs 603 may indicate to a user the type of information being displayed while the sequential illumination (i.e., number of LEDs illuminated) conveys information such as the amount of batter power remaining or the strength of a network connection. In other embodiments, indicator LEDs 603 may be substituted or combined with other components for conveying information. For example, status indicator system 600 may include one or more of a speaker, liquid crystal display, LED display, touch screen, etc.

In one embodiment, the activation of status indicator LEDs 603 functioning as battery status lights is achieved by touching the recessed surface in the handle area, where proximity sensor 605 is activated to turn on the battery status LEDs. Once touched, five LEDs indicate the battery level by the number of LEDs illuminated and the lights remain on for 3-4 seconds so that a user can see and understand the indicator to know the battery status. The LEDs are then turned off. In some embodiments, the remaining power of a backup battery may be displayed. For example, when a user activates proximity sensor 605 the remaining power of the main battery may be indicated by the number (e.g., three of five) indicator LEDs 603 illuminated with the color green. After a set amount of time (e.g., three seconds), the remaining power of the backup battery may be displayed to the user using indicator LEDs 603. Continuing the example, the remaining power of the backup battery may be indicated by the number (e.g., five of five) indicator LEDs 603 illuminated with the color yellow. In other embodiments, any of the techniques described above may be used alone or in combination to display the amount of power remaining in the main battery and the backup battery to the user of portable ultrasound system 100. In some embodiments, the battery is provided with a touch sensor (e.g., a touch sensor similar or identical to proximity sensor 605), and the activation of status indicator LEDs 603 functioning as battery status lights is achieved by touching the touch sensor provided with the battery. In various such embodiments in which the battery is provided with a touch sensor, the touch sensor and/or the status indicator LEDs 603 may be disposed on the battery, or on the battery cover, including a surface of the battery cover facing the battery or a surface of the battery cover facing away from the battery. For example, the touch sensor may be provided on the battery, and the status indicator LEDs 603 may be provided on the surface of the battery cover facing the battery, so that when the touch sensor is touched, the illumination response of the status indicator LEDs 603 on the battery cover can be clearly detected.

Figure 19:
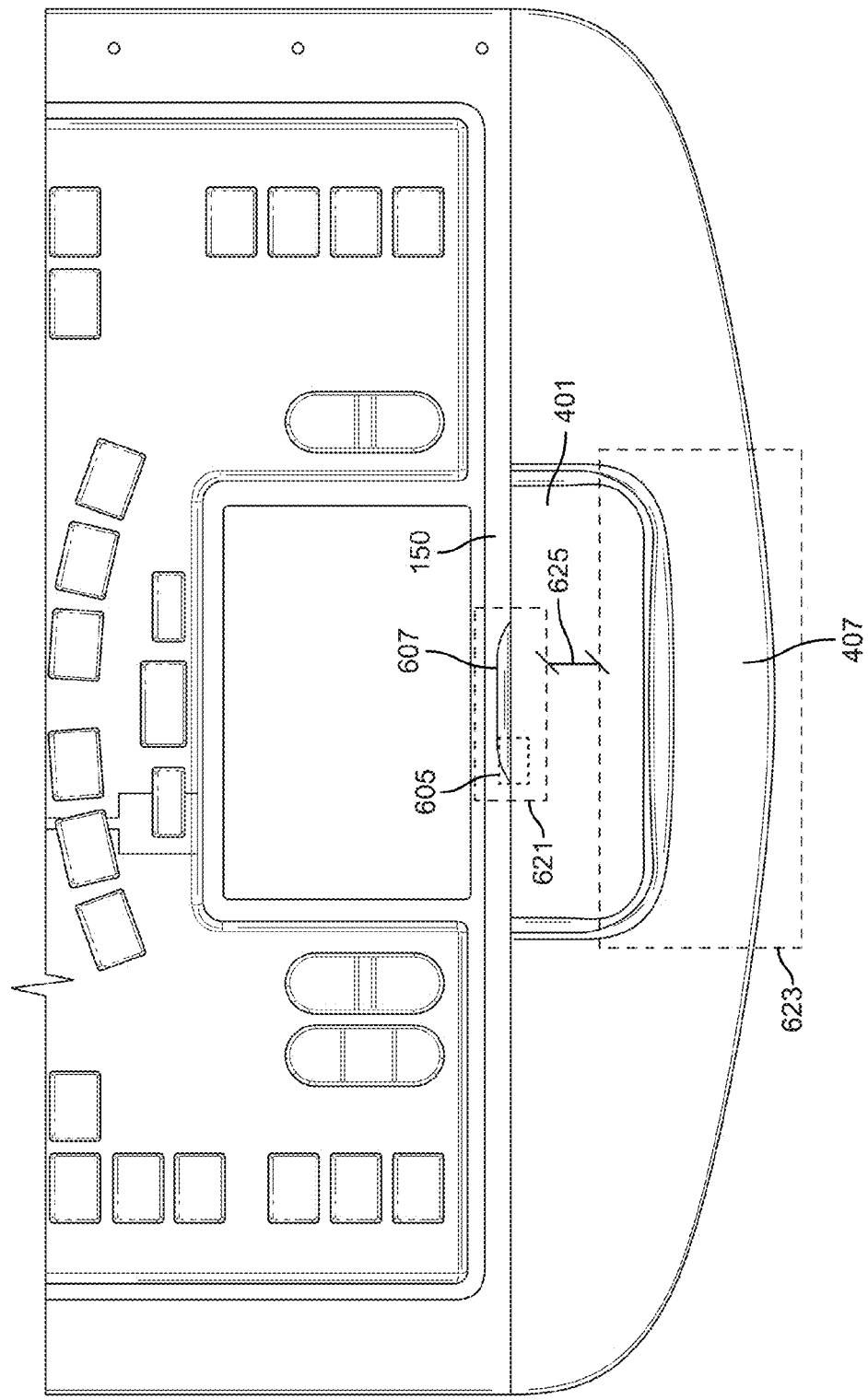
FIG. 19 illustrates an embodiment of a status indicator system including a detection zone and handle gripping zone.

FIG. 19 illustrates a top view of an embodiment of status indicator system 600. Proximity sensor 605 has a defined detection zone 621 (illustrated as a dashed line). Detection zone 621 is the area in which an object (e.g., a user's finger or hand) being present will activate proximity sensor 605. Detection zone 621 may be three dimensional extending outward from proximity sensor 605. In some embodiments, detection zone 621 matches the contours of enclosure 607 such that an object enters detection zone 621 only when it touches enclosure 607. For example, detection zone 621 may follow the contours of enclosure 607 in embodiments where proximity sensor 605 is a resistive touch sensor. Detection zone 621 may also follow the contours of enclosure 607 in embodiments where proximity sensor 605 is a capacitive touch sensor. In other embodiments (e.g., where proximity sensor 605 is a projected capacitive sensor or capacitive sensor), detection zone 621 extends beyond enclosure 607.

Detection zone 621 may be a distance 625 away from handle gripping zone 623. Handle gripping zone 623 defines the area in which part of a user's body will be when gripping handle 407. In some embodiments, detection zone 621 and handle gripping zone 623 are mutually exclusive. They are separated by a distance 625. For example, detection zone 621 may be configured such that distance 625 ensures that proximity sensor 605 is unlikely to be activated by a user grabbing handle 407. In other embodiments, detection zone 621 and handle gripping zone 623 overlap. Detection zone 621 may be configured such that when a user grips handle 407 proximity sensor 605 is activated.

Figure 20:
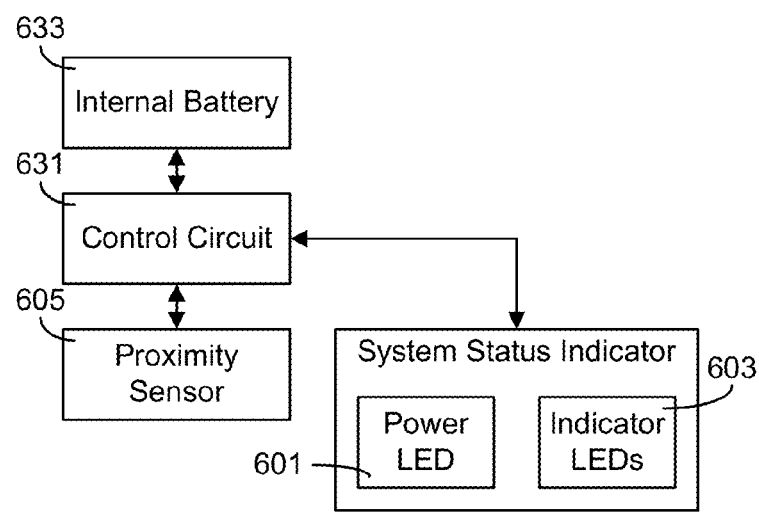
FIG. 20 illustrates a block diagram of components of one embodiment of a status indicator system.

FIG. 20 illustrates a block diagram of components of status indicator system 600 according to one embodiment. Control circuit 631 is coupled to proximity sensor 605, power LED 601, indicator LEDs 603, and internal battery 633. In some embodiments, control circuit 631 may be coupled to additional components of portable ultrasound system 100. For example, control circuit 603 may be coupled to a backup battery. Control circuit 631 may include a processor and memory. In some embodiments, control circuit 631 is part of another circuit board. For example, control circuit 631 may be part of a circuit board of portable ultrasound system 100. In further embodiments, control circuit 631 supplies power to components of status indicator system 600 (e.g., directly or through controlling access to power from a source such as a battery or power supply).

Control circuit 631 detects when an object enters proximity sensor detection zone 621 (e.g., when proximity sensor 605 is activated) using proximity sensor 605. Proximity sensor 605 sends a signal (e.g., change in voltage, output voltage, change in capacitance, change in resistance, etc.) to control circuit 631 which determines that an object (e.g., user finger) has entered proximity sensor detection zone 621. In other embodiments, control circuit 605 monitors proximity sensor 605 for a change in a parameter such as capacitance or resistance. Control circuit 631 may be configured to ignore objects in detection zone 621 as not intended to activate proximity sensor 605. For example, control circuit 631 may be configured to screen out inadvertent activation of proximity sensor 605 by the time for which an object remains in detection zone 621. Continuing the example, control circuit 631 may require an object to be detected in detection zone 621 for one second prior to displaying system status information.

In some embodiments, control circuit 631 determines what information to display (e.g., battery status or network status) based on the input from a user received through proximity sensor 605. This determination may be made using the length of time for which an object is detected in detection zone 621, the direction an object moves through detection zone 621 (e.g., left to right, down to up, etc.), a gesture performed by the user, etc. In other embodiments, a user may define through an operating system running on portable ultrasound system 100 what information is to be displayed by status indicator system 600 when proximity sensor 605 is activated. This selection may be stored in memory which is included in some embodiments of control circuit 631.

When control circuit 631 has determined that proximity sensor 605 has been activated, control circuit 631 acquires the information to be displayed to the user. For example, control circuit 631 may determine the amount of power remaining in internal battery 633. In some embodiments, control circuit 631 acquires the information to be displayed directly (e.g., through measurement and/or calculation). In other embodiments, control circuit 631 acquires the information to be displayed from another component of portable ultrasound system 100. For example, control circuit 631 may acquire the information to be displayed from a circuit board included in portable ultrasound system 100.

Control circuit 631 displays the acquired information using indicator LEDs 603 and or power LED 601. Control circuit 631 controls indicator LEDs 603 and/or power LED 601 to display information using the techniques described above. This may be carried out by providing a control signal, providing power of a certain voltage, or turning on and off LEDs. For example, the color displayed by status indicator LEDs 603 may be selected by a control signal sent from control circuit 631 to a multicolor LED. The brightness of an LED may be varied depending on the voltage supplied by control circuit 631 to power LED 601 and/or indicator LEDs 603. Control circuit 631 may supply power to indicator LEDs 603 and/or power LED 601 with a set frequency (e.g., controlled by a variable timing circuit) in order to control the frequency with which the LEDs flash.

With reference to FIG. 20 and FIG. 3A, in one embodiment, control circuit 631 is located on main circuit board 161. In other embodiments, the functions of control circuit 631 described above are carried out by processing circuit 163 on main circuit board 161. For example, processing circuit 163 may receive data from proximity sensor 605 through user input interface 173 on main circuit board 161. Processing circuit 163 may also control power LED 601 and/or indicator LEDs 603 through user input interface 173. Processing circuit 163 may acquire data regarding available battery power through power supply interface 177 and power supply board 179. Processing circuit 163 may then preform calculations or other processes to determine the amount of available battery power to be displayed using indicator LEDs 603.

In other embodiments, the above described functions (e.g., displaying strength of wireless connection) carried out by control circuit 631 may be performed with main circuit board 161 and the components therein. For example, processing circuit 163 may determine the strength of a wireless connection by acquiring data from communications interface 175 regarding wireless hardware connected to main circuit board 161. Processing circuit 163 may calculate the strength of the signal and display it to a user with indicator LEDs 603 controlled through user input interface 173 on main circuit board 161.

Figure 21:
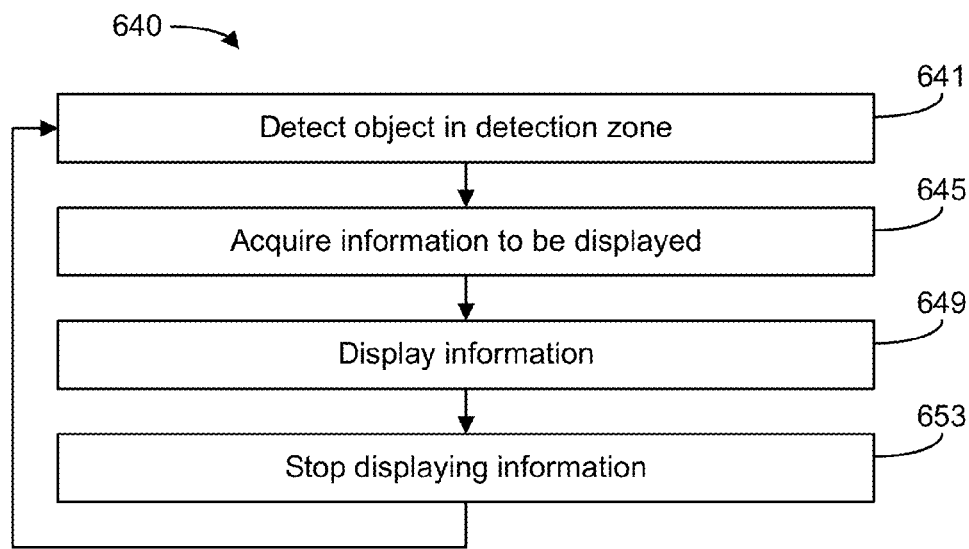
FIG. 21 illustrates a flow chart corresponding to a method of operation for one embodiment of a status indicator system.

FIG. 21 illustrates method 640 for displaying information using status indicator system 600. An object is detected (641) in detection zone 641. As explained above, the object (e.g., a user's finger or hand) may be detected with a combination of proximity sensor 605 and/or control circuit 631. Control circuit 631 may also use an algorithm to identify intentional activations of proximity sensor 605. In some embodiments, this includes requiring an object to be detected in detection zone 641 for a set amount of time. In other embodiments, control circuit 631 may apply a lockout time during which detection of an object does not trigger the display of information. For example, if a user activates proximity sensor 605 and information is displayed, control circuit 631 may not display information for five seconds regardless of a detected object. This may prevent the continuous display of information. For example, a user holding handle 407 may trigger activate proximity sensor 605 continuously. However, information may only be displayed once due to the lockout applied by control circuit 631. In other embodiments, control circuit 631 may periodically (e.g., every 30 seconds) display information when an object is continuously detected in detection zone 621. Control circuit 631 may also determine which information to display based on characteristics of the object detected (e.g., direction the object travels, the length of time for which the object is detected, etc.).

The information to be displayed is then acquired (645). Control circuit 631 may acquire this information through direct measurement or through an additional component such as a circuit board or processor. The information is displayed (649). This includes displaying the information according to the techniques described above. In some embodiments, the information is displayed for a set amount of time. For example, indicator LEDs 603 remain lit for three seconds. Control circuit 631 then stops displaying information (653). In some embodiments, a user may change this time through a user interface included in portable ultrasound system 100. In other embodiments, the information is displayed until the object which activated proximity sensor 605 leaves detection zone 621. For example, indicator LEDs 603 may remain lit until a user removes his or her finger from enclosure 607. In further embodiments, the information may be displayed for an additional time (e.g., one second) after a user has removed his or her finger from enclosure 607.

Some embodiments of portable ultrasound system 100 include a backup battery. In some embodiments, the backup battery is an internal battery. The backup battery is included within main housing 150. The backup battery may be configured to function as an uninterruptable power supply providing a steady supply of power (e.g., when mains power is unpredictable). In some embodiments, the backup battery is configured to allow for hot swapping of the main battery. The backup battery provides a temporary supply of power to portable ultrasound system 100 while a depleted main battery is removed and replaced with a charged main battery. Portable ultrasound system 100 then draws power from the new main battery. In some embodiments, a user is prompted to switch the main battery by a prompt displayed on main screen 130. In other embodiments, a user is prompted to switch the main battery or informed that the main battery is depleted by status indicator system 600. For example, indicator LEDs 603 may blink red to indicate that the main battery is depleted and should be swapped for a charged main battery. In further embodiments, additional techniques may be used to indicate that the main battery should be changed. For example, portable ultrasound system 100 may provide an audio prompt to a user to change the main battery, haptic feedback may be provided by a vibration motor, etc. In some embodiments, multiple techniques may be used to indicate that the main battery should be swapped.

In some embodiments, portable ultrasound system 100 enters a standby mode when the main battery is depleted. Portable ultrasound system 100 may continue to run or shut down in an orderly fashion while running on power provided by the backup battery. Advantageously, this allows portable ultrasound system 100 to prevent the loss of data when the main battery is depleted. In further embodiments, portable ultrasound system 100 enters a standby mode prior to the hot swapping of the main battery. In other embodiments, the main battery of portable ultrasound system 100 may be hot swapped without portable ultrasound system 100 first entering a standby mode. During the hot swapping of the main battery, the backup battery may provide power to portable ultrasound system 100.

In some embodiments, the backup battery is integrated with the power system of portable ultrasound system 100. The backup battery may be recharged from a main battery automatically without input from the user. This allows the backup battery to be charged for future use without input from a user. In some embodiments, the backup battery is configured to be replaceable (e.g., through an access panel in main housing 150). This allows the backup battery to be replaced when it is no longer capable of holding sufficient power for satisfactory hot swapping of the main battery or is no longer capable of functioning as an uninterruptable power supply (e.g., the backup battery has reached its maximum effective number of discharge cycles). The backup battery as just described enhances the portability of portable ultrasound system 100 by allowing for extended battery operation (e.g., by using multiple charged batteries). The backup battery also enhances portability of the device by functioning as an uninterruptable power supply thereby allowing operation in areas with unreliable mains power. Additionally, the backup battery provides a power source to prevent loss of data and provide power for an orderly shutdown of portable ultrasound system 100 in the event of a loss of power.

In other embodiments, the backup battery is a battery which is stored within main housing 150 but is not connected to the power system of portable ultrasound system 100. The backup battery is stored in housing 150 for the convenience of the user. When the main battery is depleted, the user may remove the main battery, remove the backup battery from housing 150 and insert the backup battery. The user may then store the depleted main battery in housing 150 in the area formerly holding the backup battery. The depleted main battery may be stored within housing 150 until a user is able to charge it.

Referring generally now to FIGS. 17-21, portable ultrasound system 100 includes a second status indicator system 600 in some embodiments. The second status indicator system 600 can be used to display information related to a replaceable or backup battery of portable ultrasound system 100. In one embodiment, second status indicator system 600 is included in a battery cover or near a portion of portable ultrasound system 100 used to receive the battery. Enclosure 607 can be included in or on the battery cover. In other embodiments, enclosure 607 can be included near the location of the battery when inserted (e.g., enclosure 607 can be in or on main housing 150). Proximity sensor 605 can be triggered by a user which causes the display of battery charge level via indicator LEDs 603 and/or power LED 601. In some embodiments, a first status indicator system 600 and the second status indicator system 600 share one or more components. For example, a single control circuit 631 may control both systems. The second status indicator system 600 can include separate indicator LEDs 603, proximity sensor(s) 605, and/or power LED 601. The single control circuit 631 can distinguish between both systems and process inputs and control outputs according to which system is activated by a user. In alternative embodiments, second status indicator system 600 includes separate components.

In one embodiment, a replaceable battery module (e.g., a main battery and/or backup battery which can be swapped for one another) includes the second stats indicator system 600. Proximity sensor 605 can be triggered by a user which causes the display of battery charge level via indicator LEDs 603 and/or power LED 601. One or more components of the second status indicator system 600 can be housed in an enclosure 607 located on or in the backup battery. The second status indicator system 600 can further include control circuit 631. The second status indicator system 600 can be powered by the battery in/on which second status indicator system 600 is included.

Advantageously, a second status indicator system 600 (e.g., included in a battery and/or in portable ultrasound system 100) allows a user to quickly check battery charge level without having to depress a button or lever. Additionally, second status indicator system 600 provides an advantage in that second status indicator system 600 operates similarly or the same as status indicator system 600 located elsewhere (e.g., in ergonomic handle system 400) thereby simplifying use of portable ultrasound system 100. A consistent user model is provided that simplifies a user's understanding of portable ultrasound system 100. Second status indicator system 600 can replace physical levers, latches, buttons, or other components which a user would otherwise have to actuate to check the status of a battery. Therefore, physical parts which can become compromised due to dirt or liquids are replaced in part or entirely with second status indicator system 600 thereby providing an advantage.

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for displaying status information related to a portable device, comprising:
   detecting a portion of a user in a detection zone using a proximity sensor;
   determining, using a control circuit, that the portable device is in a powered off or power saving state;
   acquiring, using the control circuit, information about the portable device while the portable device remains in the powered off or power saving state;
   displaying, using a system status indicator controlled by the control circuit, a representation of the information about the portable device,
   wherein the detection zone is defined in relation to a handle of the portable device.

2. The method of claim 1, wherein at least one of the proximity sensor or the system status indicator are located within a concave enclosure positioned on a main housing of the portable device, the concave enclosure positioned to provide a recessed area in which the user places one or more fingers to grip a lid of the portable device while opening the lid, and wherein the detection zone is configured to detect the one or more fingers of the user when the user opens the lid of the portable device.

3. The method of claim 1, wherein the proximity sensor and the system status indicator are located within a handle cutout of the handle, the handle cutout configured to receive a hand of the user for carrying the portable device.

4. The method of claim 3, wherein at least one of the proximity sensor or the system status indicator are located within an enclosure positioned on a main housing of the portable device, within handle cutout, and opposite a portion of the handle configured to be gripped by the user, and wherein the enclosure is one of substantially a recessed partial hemisphere or substantially a raised partial hemisphere.

5. The method of claim 3, wherein the detection zone is configured such that when a user grips the handle the proximity sensor is activated.

6. The method of claim 1, wherein the information about the portable device includes at least one of an amount of remaining battery power available to the portable device, an amount of remaining backup battery power available to the portable device, a network connection status, a remaining time to complete charging of a battery of the portable device, an amount of available memory for data storage, a strength of a wireless network connection, or an indication of power state of the portable device.

7. The method of claim 1, wherein the system status indicator includes a plurality of light emitting diodes, and wherein the control circuit controls at least one of the number of illuminated light emitting diodes or the color of at least one of the light emitting diodes to display the representation of the information about the portable device.

8. The method of claim 1, further comprising:
determining that the information about the portable device has been displayed using the system status indicator for a predetermined amount of time; and
in response:
- ceasing to display the information about the portable device using the system status indicator, and
- preventing further display of information about the portable device using the system status indicator until (A) after a predetermined amount of time or (B) the user is no longer detected by the proximity sensor.

9. A portable device, comprising:
- a proximity sensor having a detection zone defined in relation to a handle of the portable device;
- a system status indicator configured to display information; and
- a control circuit coupled to the proximity sensor and the system status indicator, configured to receive input from the proximity sensor indicating that a portion of a user has been detected in the detection zone, determine that the portable device is in a powered off or power saving state, acquire information about the portable device or a subsystem thereof while the portable device remains in the powered off or power saving state, and display a representation of the acquired information via the system status indicator.

10. The portable device of claim 9, wherein at least one of the proximity sensor or the system status indicator are located within a concave enclosure positioned on a main housing of the portable device, the concave enclosure positioned to provide a recessed area in which the user places one or more fingers to grip a lid of the portable device while opening the lid, and wherein the detection zone is configured to detect the one or more fingers of the user when the user opens the lid of the portable device.

11. The portable device of claim 9, wherein at least one of the proximity sensor or the system status indicator are located within an enclosure positioned on a main housing of the portable device, within a handle cutout, and opposite a portion of the handle configured to be gripped by the user, and wherein the enclosure is one of substantially a recessed partial hemisphere or substantially a raised partial hemisphere.

12. The portable device of claim 9, wherein the proximity sensor and the system status indicator are located within a handle cutout of the handle, the handle cutout configured to receive a hand of the user for carrying the portable device, and wherein the detection zone is configured such that when a user grips the handle the proximity sensor is activated.

13. The portable device of claim 9, wherein the information about the portable device includes at least one of an amount of remaining battery power available to the portable device, an amount of remaining backup battery power available to the portable device, a network connection status, a remaining time to complete charging of a battery of the portable device, an amount of available memory for data storage, a strength of a wireless network connection, or an indication of power state of the portable device.

14. The portable device of claim 9, wherein the system status indicator includes a plurality of light emitting diodes, and wherein the control circuit is configured to control at least one of the number of illuminated light emitting diodes or the color of at least one of the light emitting diodes to display the representation of the information about the portable device.

15. The portable device of claim 9, wherein the control circuit is further configured to determine that the information about the portable device has been displayed using the system status indicator for a predetermined amount of time, and in response to the determination cease the display of the information about the portable device via the system status indicator, and prevent further display of information about the portable device using the system status indicator until (A) after a predetermined amount of time or (B) the user is no longer detected by the proximity sensor.

* * * * *